United States Patent [19]
Gerhardt et al.

[11] Patent Number: 5,806,517
[45] Date of Patent: Sep. 15, 1998

[54] IN VIVO ELECTROCHEMISTRY COMPUTER SYSTEM AND METHOD

[75] Inventors: Greg Allen Gerhardt, Denver; Steven Alan Robinson, Aurora, both of Colo.

[73] Assignee: The Regents of the University of Colorado, Boulder, Colo.

[21] Appl. No.: 452,161

[22] Filed: May 26, 1995

[51] Int. Cl.$^6$ ........................................... A61B 5/05
[52] U.S. Cl. ............................................. 128/635
[58] Field of Search ................... 128/631–635, 128/639, 642, 731

[56] References Cited

U.S. PATENT DOCUMENTS

| | | | |
|---|---|---|---|
| 4,883,057 | 11/1989 | Brederick | 128/631 |
| 5,443,710 | 8/1995 | Broderick | 128/635 X |
| 5,551,425 | 9/1996 | Essen-Moller | 128/635 |

OTHER PUBLICATIONS

Article "Nafion–Coated Electrodes with High Selectivity for CNS Electrochemistry" By G. A. Gerhardt et al, Brain Research, 290 (1984) pp. 390–395.

"Effects of Electrical Stimulation of Brain Reward Sites On Release of Dopamine in Rat: An In Vivo Electrochemical Study" By A. Gratton et al, Brain Res. Bulletin, pp. 319–324.

"In Vivo Electrochemical Studies of Monomine Rel. In the Medical Prefrontal Cortex of the Rat" by A. Gratton et al, Neuroscience, vol. 29, #1, pp. 57–64, 1989.

"In Vivo Electrochemical Measurements and Electrophysiological Studies of Rat Striatum Following Neonatal 6–Hydroxydopamine Treatment" J. Luthman et al from Neuroscience, vol. 52, No. 3, pp. 677–687, 1993.

Age induced changes in single locus coeryleus brain transplants grown in aculo: An in vivo electrochemical sturdy G. A. Gerhardt et al from Neurobiology of Aging, vol. 12, 1991, pp. 487–494.

"Electrochemical characterization of stimulated noreplaephrine overflow in Locus coeruleus–hippocanpus double brain grafts grown in oculo" Neuroscience Letters 110 (1990) pp. 186–192 by Mei–Tsu Su et al.

"Regional Effects of Aging on Dopaminergic Function In the Fischer–344 Rat" By M. Friedemann et al, Neurobiology of Aging, vol. 13, pp. 325–332, 1992.

Experimental Neurology 122, 1993, By J. Luthman et al, pp. 273–282 "In Vivo Electrochemical Measurements of Exogenous Dopamine Clearance in Normal and Neonatal 6–Hydroxydopamine–treated Rat Striatum".

*Primary Examiner*—Jennifer Bahr
*Assistant Examiner*—Samuel Gilbert
*Attorney, Agent, or Firm*—Earl C. Hancock; Francis A. Sirr; Holland & Hart llp

[57] ABSTRACT

A chemical detection and analysis system performs chemical measurements using microsensors. The in vivo or in vitro system records chemical concentrations of any substance that can be oxidized or reduced at the sensor surface in response to a voltage waveform applied to a reference electrode. The electrochemical technique has utility relative to molecules that are electroactive. Diffusion and metabolism of these chemicals are tracked in real time. A visual display of the measurements is provided in near real time. The system consists of: a 32 bit, digital computer; application software; an I/O board with analog to digital convertors, digital to analog converters, and digital input/output capability; a potentiostat; one to four microsensors; and a reference electrode. Calibrated microsensors, of carbon, platinum, or gold, are placed in brain tissue or other aqueous environments to detect chemical activity. A reference electrode is placed in the tissue at a location that is spaced from the sensors. A pulse cyclic or a constant electrical potential is generated and applied to the reference electrode to induce an oxidation or reduction current condition at the sensor surface. Calibration of the sensors, acquisition and storage of data, and auto-analysis of data, as well as user defined data analysis and modification, are performed under control of application software and hardware.

19 Claims, 23 Drawing Sheets

FAST CYCLIC VOLTAMMETRY, HARDWARE/ELECTRODE TIMING

[<——] LEFT ARROW INCREASES DELAY
[——>] RIGHT ARROW DECREASES DELAY
[ENTER] CLEARS WINDOW
[ESC] RETURN TO MENUE

INCORRECT HARDWARE SETTING

FAST CYCLIC VOLTAMMETRY, HARDWARE/ELECTRODE TIMING

[<——] LEFT ARROW INCREASES DELAY
[——>] RIGHT ARROW DECREASES DELAY
[ENTER] CLEARS WINDOW
[ESC] RETURN TO MENUE

CORRECT HARDWARE SETTING

CHRONOAMPEROMETRY CALIBRATION

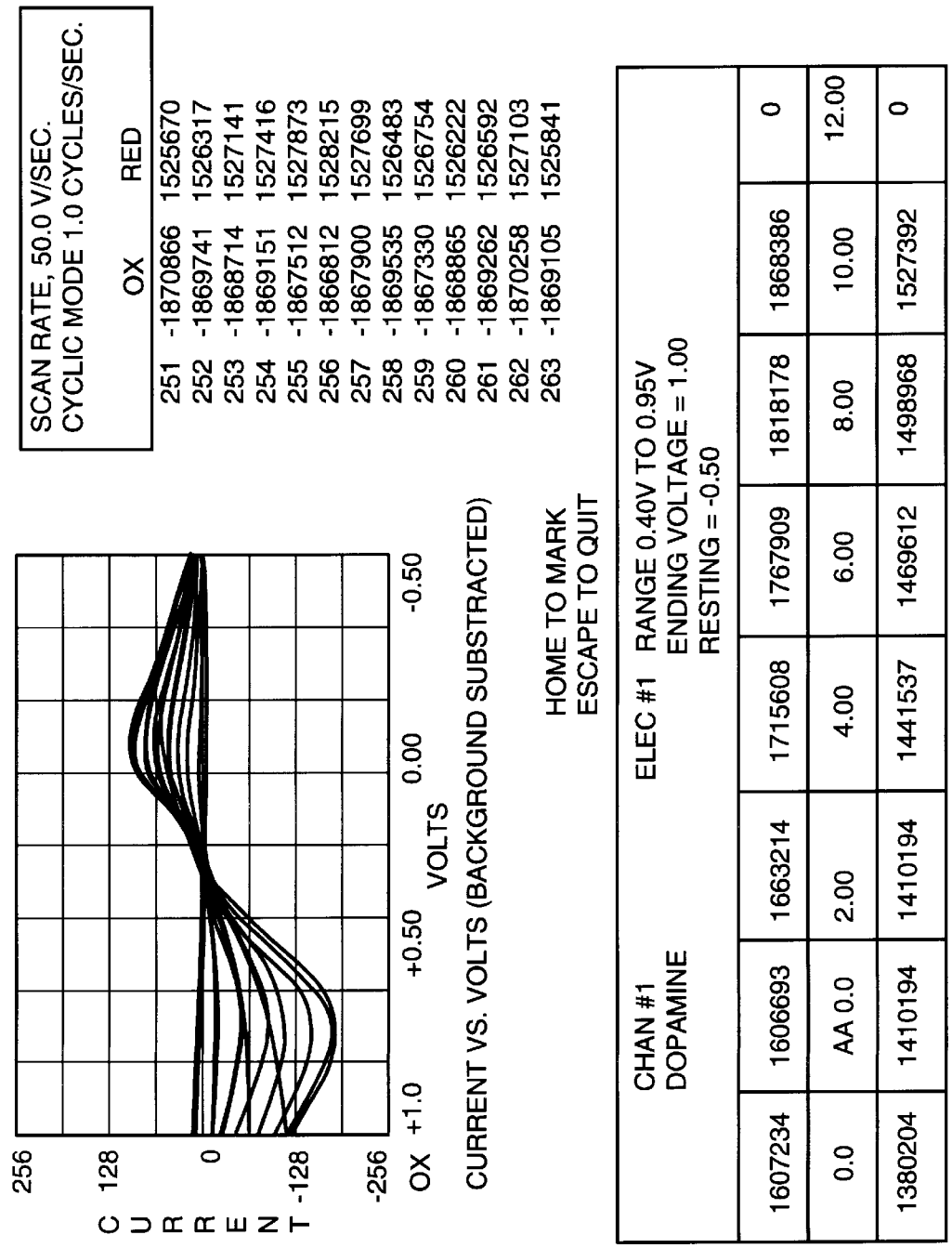

ELECTRODE VERIFICATION SCREEN (CHRONOAMPEROMETRY)

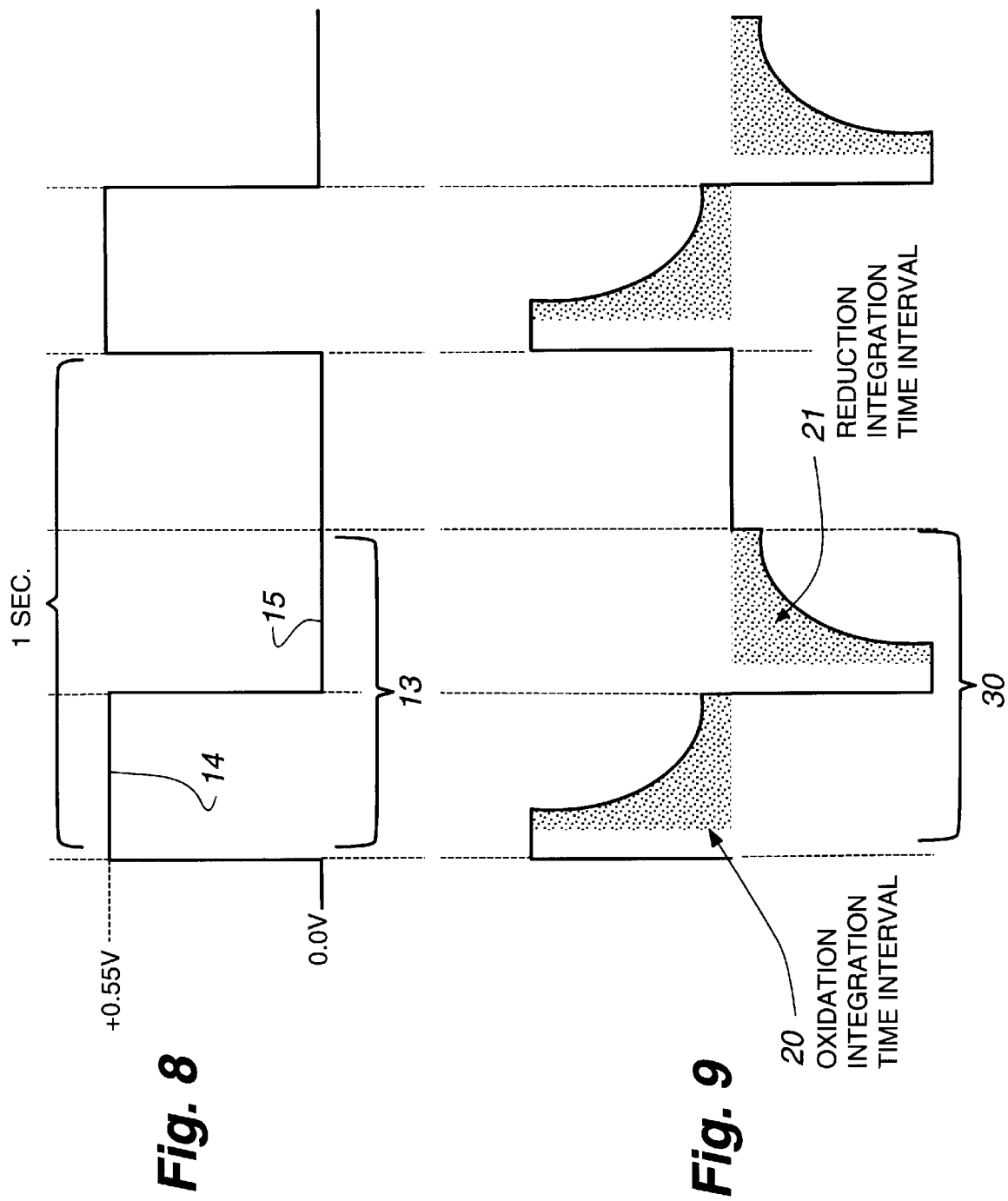

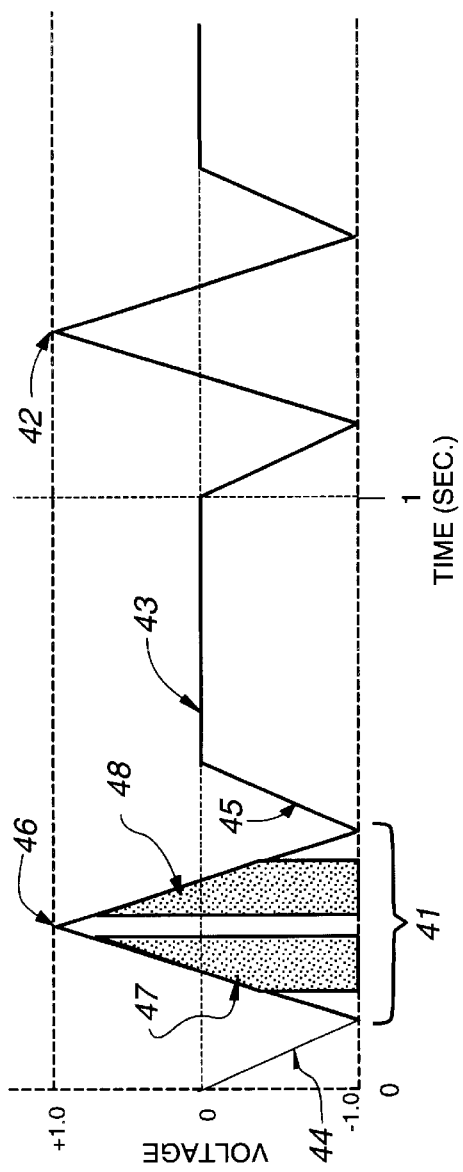
Fig. 12
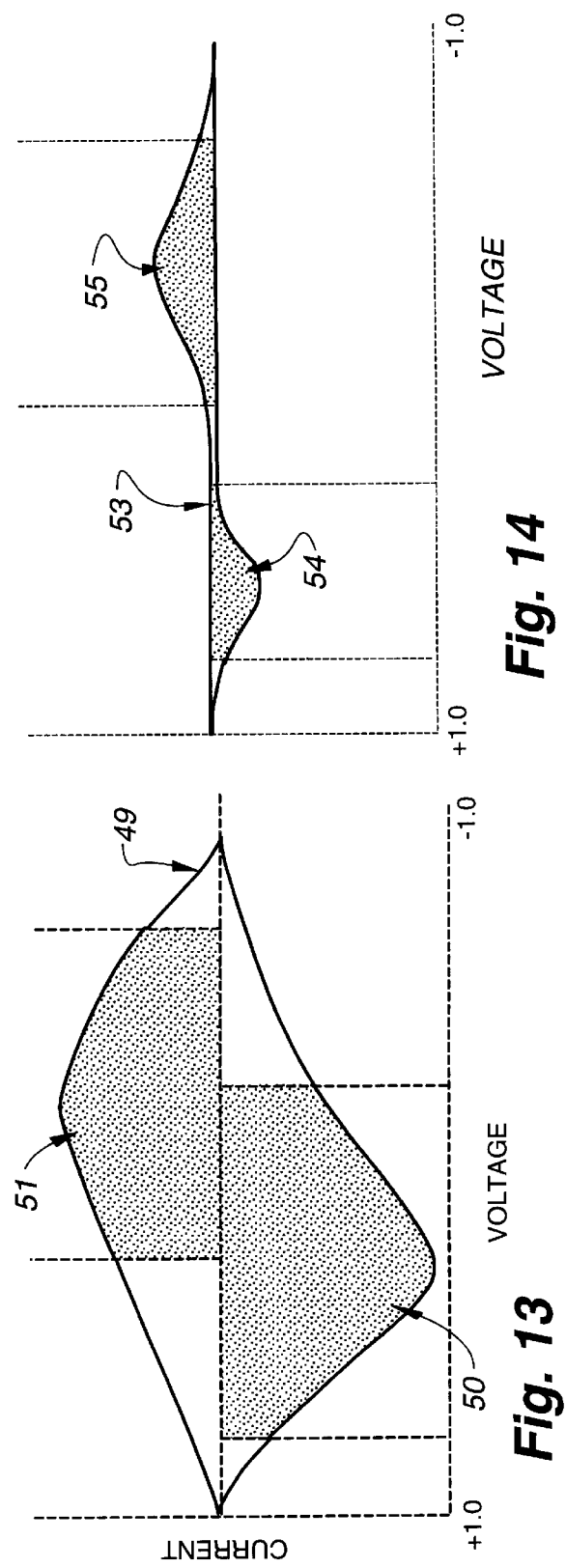
Fig. 14
Fig. 13

Fig. 16 FREQUENCY MODULATION

GRAPHIC ANALYSIS OF A RESPONSE

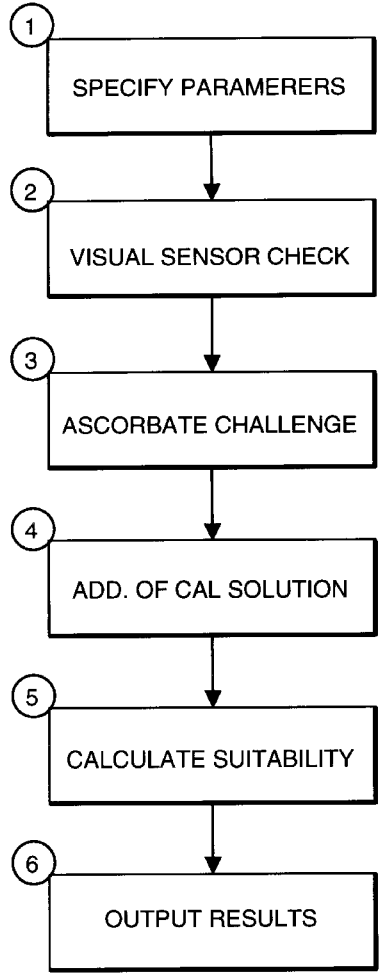
Fig. 22 CALIBRATION PROGRAM
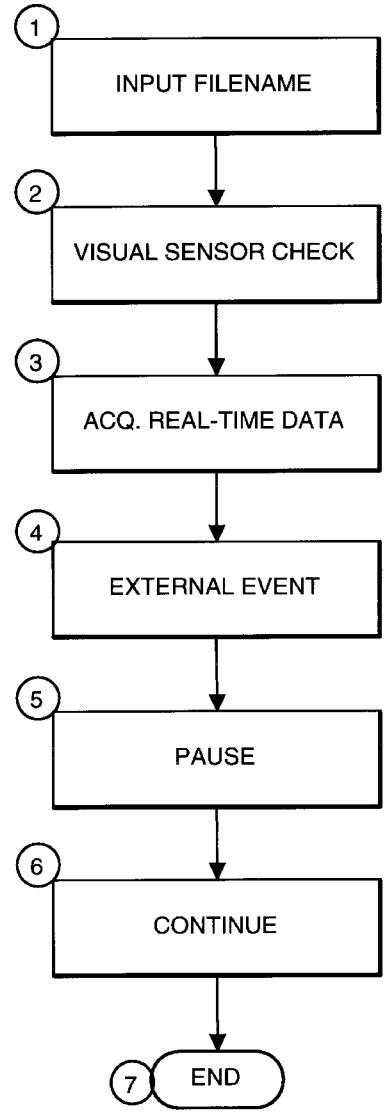
Fig. 23 DATA ACQUISITION

ANALYSIS AND EDIT

| TOTAL NUMBER OF RELEASES #37 | | |
|---|---|---|
| RELEASE NUMBER | | 20 |
| OX PEAK AREA | | 9895 |
| AMPLITUDE | | 5.42 |
| SIGNAL/NOISE | | 0.49737 |
| HYSTERESIS | 0 MIN | 37 SEC |
| RED/OX RATIO | | 0.53 |
| RISE TIME | 0 MIN | 11 SEC |
| T20 | 0 MIN | 16 SEC |
| T40 | 0 MIN | 19 SEC |
| T50 | 0 MIN | 20 SEC |
| T60 | 0 MIN | 23 SEC |
| T80 | 0 MIN | 30 SEC |
| T90 | 0 MIN | 38 SEC |
| T20-60 | 0 MIN | 7 SEC |
| T40-80 | 0 MIN | 11 SEC |
| Tc | 0.3094 μM/SEC | |
| TIME COURSE | 1.0 MIN | 15 SEC |

Labels: 901 → RELEASE NUMBER; 902 → AMPLITUDE; 903 → SIGNAL/NOISE; 904 → HYSTERESIS; 905 → RED/OX RATIO; 906 → RISE TIME; 907 → T20; 908 → T40; 909 → T50; 910 → T60; 911 → T80; 912 → T90; 913 → T20-60; 914 → T40-80; 915 → Tc; 916 → TIME COURSE

TABULATED RELEASE DATA

*Fig. 25*

IN VIVO ELECTROCHEMISTRY COMPUTER SYSTEM AND METHOD

This invention was made with Government support under contract BNS 9220308 awarded by the National Science Foundation. The Government has certain rights in this invention.

BACKGROUND OF THE INVENTION

1. Field of the Invention

This invention is concerned with a system and method for data acquisition and data processing particularly dedicated to neurological medical-type applications. The invention is specifically intended to detect and analyze neurotransmitters that are associated with the nervous system of animals or humans. The invention has wide utility and is particularly applicable to brain tissue studies, nervous system-related data acquisition, neurosurgery support, and the like.

2. Description of the Related Art

The use of electrodes to detect electro-oxidizable species in brain extracellular fluid is generally known. For example, the publication *Brain Research*, 290(1984) at pages 390–395 describes a very small graphite electrode that is coated with Nafion (Dupont) perfluorosulfonated polymer in order to improve the selectivity of the electrode.

The publication *Brain Research Bulletin*, Vol. 21, at pages 319–324, copyright Pergamon Press pic. 1988, describes the use of stainless steel electrodes that are implanted in the brain of rats and then energized to electrically stimulate the brain cells, to thereby determine the effects of electrical stimulation on the release of dopamine, thereby providing a study of what happens to neurons in this situation.

The publication *Neuroscience*, Vol. 29, No. 1, at pages 57–64, 1989, describes an in vivo method of studying monoamine release in rats wherein a Nafion coated graphite electrode received an oxidation potential of plus 0.55 volts for 100 ms at a rate of 5 Hz. The resulting oxidation current was digitally integrated during the last 60 ms of the pulse. The reverse current flow generated by the reduction of the oxidized electroactive species was digitized when the potential was dropped back to its resting level of minus 0.2 volts for 100 ms.

The publication *Neuroscience Letters*, 110(1990) at pages 186–192 describes a high speed in vivo electrochemical recording method using a Nafion coated carbon fiber electrode. Square wave pulses of 0.0 to plus 0.55 volt were applied for 0.2–1.0 s, and the resulting oxidation and reduction currents were digitally integrated during the final 60–80% of the recording period.

The publication *Neurobiology of Aging*, Vol. 12, at pages 487–494, copyright Pergamon Press plc 1991, describes the use of Nafion coated carbon fiber electrodes and square wave pulses of 0.0 to plus 0.55 volt applied for 0.1 s, repeated five times a second. The resulting oxidation and reduction currents were digitally integrated during the final 70% of the recording period.

The publication *Neurobiology of Aging*, Vol. 13, at pages 325–332, 1992, describes the use of graphite-epoxy capillary electrodes and carbon fiber electrodes wherein measurements were taken at five Hz, and then averaged over 1 s. A potential of plus 0.55 volts was applied to the electrode for 100 msec. The resulting oxidation current was digitally integrated during the last 70 msec of the pulse. When the electrode was returned to its resting potential of 0.0 volts, the reduction current produced by the oxidized electrode species was integrated in the same manner.

The publication *Experimental Neurology* 122, at pages 273–282 (1993) describes use of a Nafion coated graphite-epoxy electrode wherein an oxidation potential of plus 0.55 volts was applied at a rate of five Hz. The resulting oxidation current was digitally integrated during the final 70 ms of the 100 ms pulse. The reduction current was digitized in the same manner when the potential was dropped back to its resting level of 0.0 volts for 100 ms.

The publication *Neuroscience*, Vol. 52, No. 3, at pages 677–687, 1993, describes the use of Nafion-coated graphite-epoxy capillary electrodes and carbon fiber electrodes wherein recordings at the rates of five to twenty five times per second were performed. An oxidation potential of plus 0.45 volts square wave was applied for 100 ms at a rate of five Hz. The resulting oxidation current was digitally integrated during the last 70% of the pulse. The current generated during the reduction of the oxidized electroactive species was digitized in the same manner when the potential was dropped back to its resting level of 0.0 or minus 0.2 volts for 100 ms.

While the art, as exemplified above, is generally satisfactory for the invented limited purposed, the need remains in the art for an apparatus and method for measuring neurotransmitter chemical activity in living tissue by placing a microsensor that is responsive to neurotransmitter chemical activity at a location within the tissue, wherein a pulse, cyclic, or constant electric potential is applied to a reference electrode to alternately produce a chemical oxidation condition and then a chemical reduction condition in the tissue adjacent to the microsensor, and the neurotransmitter chemical and/or its concentration is thus automatically determined.

The above-described inventive arrangement, when compared to prior devices, is simple in its construction, is easy to use, is more versatile, provides improved performance, and does not require off-line analysis by the user after the acquisition of data, the present invention providing automatic analysis of the real time acquired data and automatically providing an analysis output to the user in near real time.

SUMMARY OF THE INVENTION

This invention provides real time quantitative and qualitative analysis of a wide range of chemicals and other electroactive molecules that are produced and utilized in living tissue. Nonlimiting examples of the utility of this invention are in neurochemical research, clinical neurology, early detection of cancer, and detection of chemicals in a fluid environment such as the open ocean.

This invention is capable of detecting neurotransmitters (i.e., chemicals such as dopamine, norepinephrine, and serotonin) as they are produced by, or injected into, living tissue. The diffusion and metabolism of these chemicals are tracked in vivo (i.e., in living animals or cell systems) as it occurs in real time. Electroactive substances such as dopamine, norepinephrine, apomorphine, serotonin, acetaminophen (Tylenol), oxygen, ascorbic acid, hydrogen-peroxide, and nitric oxide can be detected and measured using this invention. While measurements are made in real time, a visual display of the measurement result is automatically provided in near real time, this display being provided in a manner such that interference does not occur with the real time measurements.

As used herein, the term "neurotransmitter" means any chemical that aids in transmitting impulses between two living nerve cells, or between a nerve cell and a muscle cell.

Nonlimiting examples of such chemicals are acetylcholine, dopamine, norepinephrine and serotonin.

As used herein, the phrase "near real time display" means a lapse in time of about 400 milliseconds, or less, behind a real time measurement.

The microsensors used in this invention are of conventional and well-known design. Generally speaking, these microsensors are in the range of from about 8 microns to about 100 microns in diameter. These microsensors are placed in specific tissue or brain areas, and cause minimal damage thereto. The sensors are capable of detecting chemical activity in very small areas and within cellular structures themselves. This invention works well with a wide variety of sensors, including without limitation thereto, carbon fiber, carbon films, diamond films, platinum, gold, iridium, and semiconductor based sensor probes.

Each sensor to be used in the system of the invention is first calibrated with the chemical of interest, and the calibration results or values for that specific sensor are stored for later analysis use, during which later use the calibration data is compared with sensed data that is acquired by use of the particular sensor. The sensor calibration feature of the invention involves calibrating the microsensors by measuring sensor response to a chemical solution of known concentration that is similar or identical to the chemical of interest, as found in living tissue or other aqueous environments. The sensors are subjected to increasing concentration increments of the particular neurotransmitter that is of interest. For acceptable sensors, the sensor's response is substantially linear as a function of equal additional increments of the neurotransmitter of interest. This calibration procedure also provides information relative to the quality of the sensor (i.e., sensitivity, selectivity, linearity), relative to the levels of chemical concentration to which the sensor is subjected. While not required by the invention, in a preferred embodiment of the invention only sensors having linear output characteristics are used, nonlinear sensors being discarded.

The electrochemical activity being measured by the invention is measured in real time at the exterior physical surface of the sensor(s) as the molecules of the chemical of interest actually come into contact with the exterior surface of the sensor(s).

In accordance with the invention, a pulse, cyclic, or constant electrical potential is applied to the sensor(s) relative to a reference electrode. This potential operates to first induce an oxidation condition, and then a reducing condition at the surface of the sensor. Any electrochemical present is measured at the surface of the sensor(s) as the electrochemicals come into physical contact with the sensor(s). This electrochemical activity is measured and recorded during both the oxidation and reduction portions of the applied electrical potential.

Chemical activity data is gathered in real time by the computer system. The sensor(s) and the reference electrode are connected to a potentiostat that is controlled by the computer system. A CRT is attached to the computer system to visually display the data in graphical format and in near real time.

The pulse, cyclic, or constant application of the electrical potential to the reference electrode is controlled by the computer system and is accomplished from once per second to many times per second. The pulse cyclic or pulsing rate of this potential is an operating parameter that is programmed into the computer system by the user. Each waveform potential that is generated by the computer system is sampled at the rate of from about 50 Khz to about 200 Khz (i.e., 50,000 to 200,000 times per second). The oxidation and reduction portions of the potential waveforms are measured separately, and the sum of the measurements of each portion comprise a measure of the response of the sensor(s) to this chemical.

The modes of operation of the invention include applying various potential or voltage waveforms to the reference electrode, including but not limited to square wave, triangular wave, constant potential, and "W" shaped waveforms. In addition, voltage frequencies, amplitudes and display rates are user selectable.

These and other objects, advantages and features of the invention will be apparent to those of skill in the art upon reference to the following detailed description of the invention, which description makes reference to the drawing.

BRIEF DESCRIPTION OF THE DRAWINGS

FIG. 1b shows the simple construction and arrangement of the present invention for comparison to the complex prior art device of FIG. 1a.

FIGS. 3a and 3b show calibrations that are performed with a chronoamperometeric waveform and with a fast cyclic voltameteric waveform, respectively, as displayed on the CRT of FIG. 1c.

FIG. 8 shows an example of a computer generated chronoamperometric waveform that is output by the D/A converter and the potentiostat to be applied to the reference electrode of FIG. 1c.

FIG. 9 shows an example of the A/D sensor signal that results from the applied electrical potential of FIG. 8, FIG. 9 also showing the preferred area of the signal waveform to be sampled and integrated in order to measure the sensor's oxidative and reductive states.

FIG. 12 shows a computer generated W shaped, or cycle and a half, voltammagram that is output by the D/A converter and the potentiostat to the reference electrode of FIG. 1c, FIG. 12 also showing the corresponding area of the W shaped wave to be integrated by the apparatus of FIG. 1c.

FIG. 13 shows an example of the A/D sensor signal that results from the applied electrical potential of FIG. 12, FIG. 13 also showing the preferred area of the A/D signal waveform to be sampled and integrated in order to measure the sensor's oxidative and reductive states.

FIG. 14 shows the waveform of FIG. 13 after the background signal has been subtracted therefrom, whereby the two areas of response to the chemical of interest are then more apparent.

FIG. 22 is a flowchart of the calibration procedure in the application software of FIG. 21 and the computer system of FIG. 1c.

FIG. 23 is a flowchart of the data acquisition procedure in the application software of the computer system of FIG. 1c.

FIG. 25 shows the tabular output of the automated analysis engine of FIG. 20, which engine receives as inputs the calibration data provided by FIG. 4 and an input data file, this being the response of a sensor to chemical activity as is provided by operation of the apparatus of FIG. 20, and as displayed on the CRT of FIG. 1c.

DESCRIPTION OF THE PREFERRED EMBODIMENT

Figure 1A:
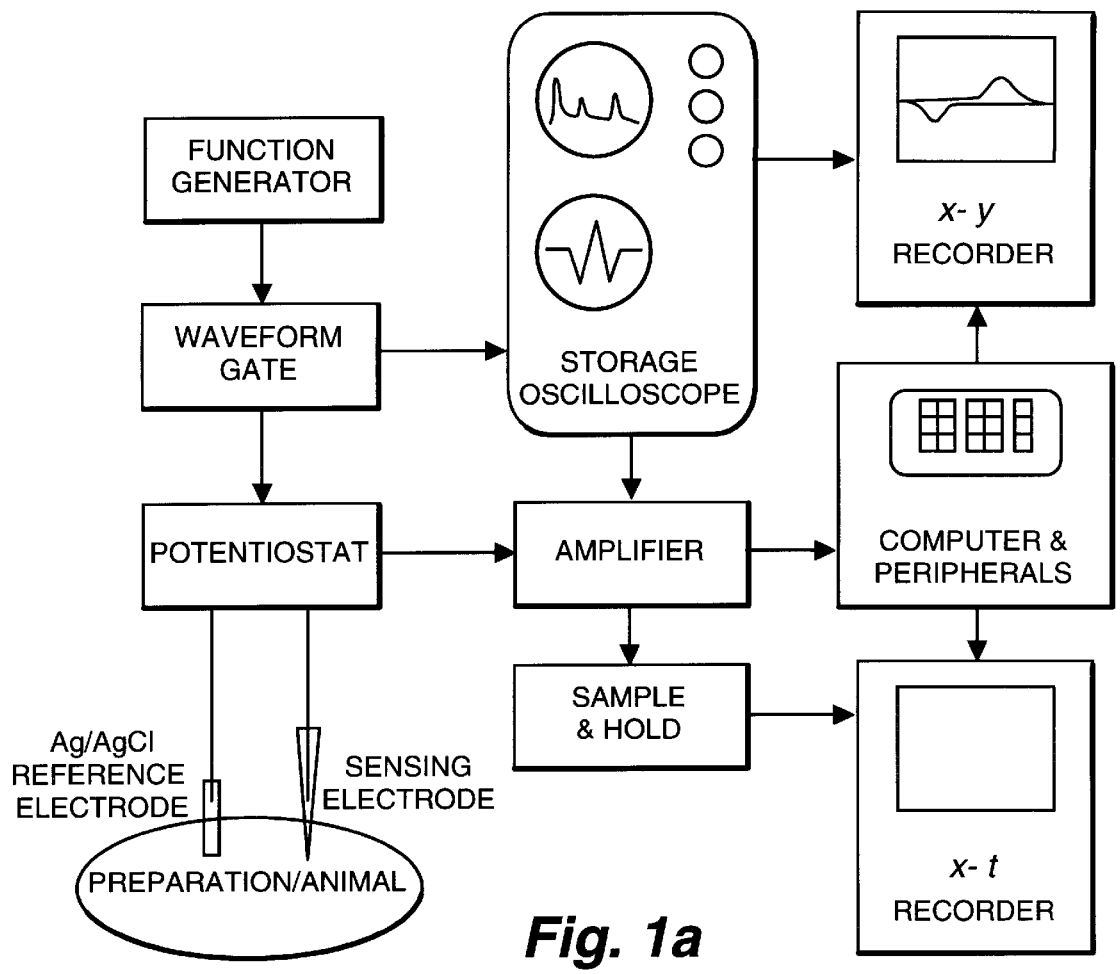
FIG. 1a shows the complex construction and arrangement of a related prior art device.
Figure 1B:
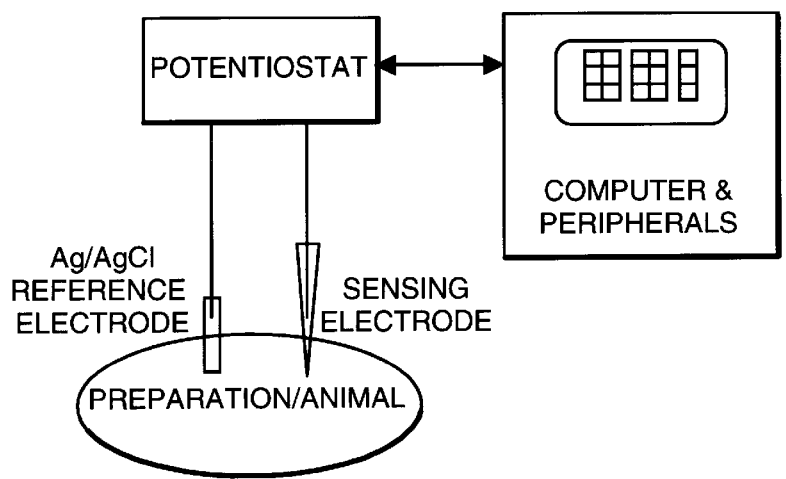
Figure 1C:
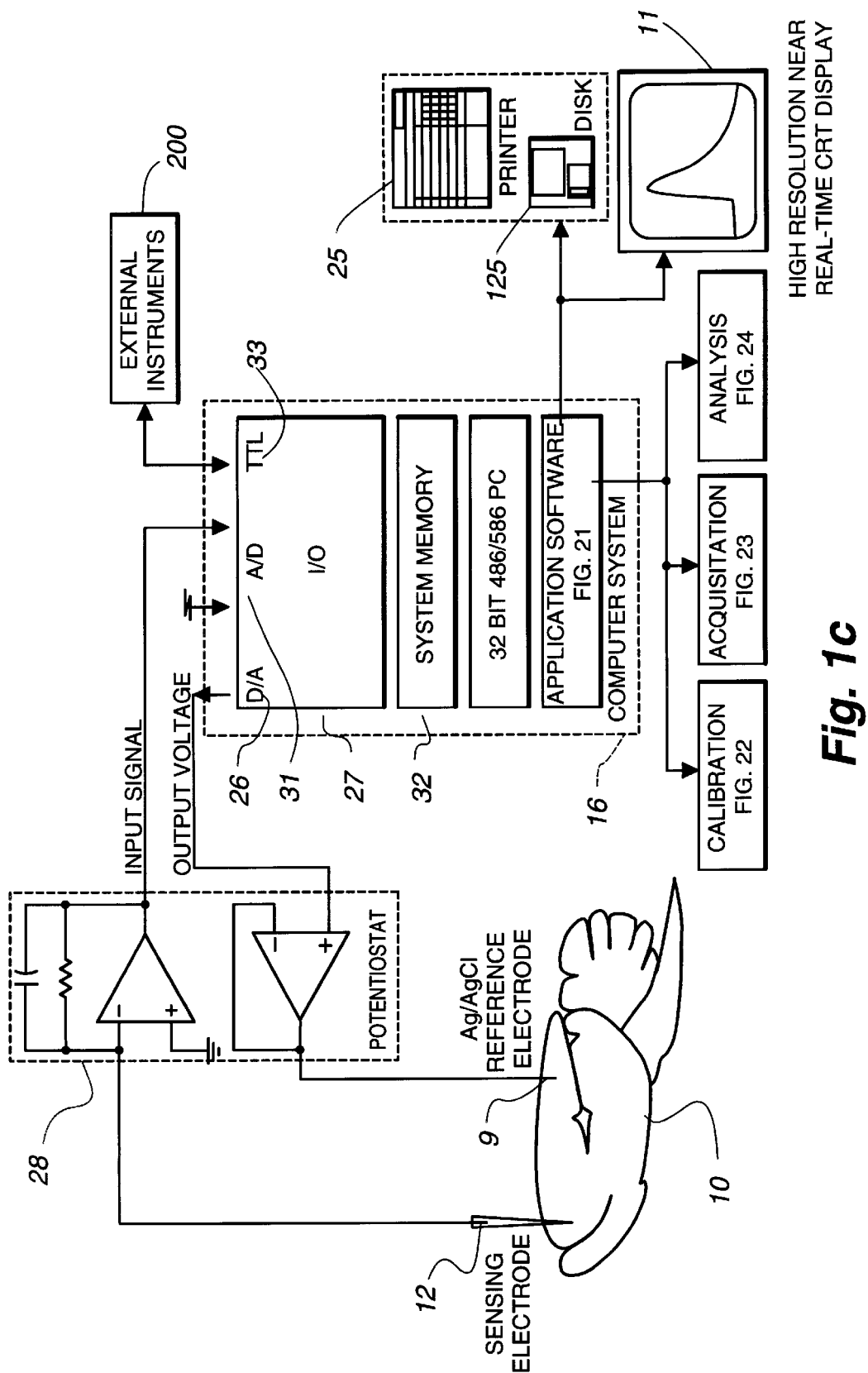
FIG. 1c shows apparatus of the invention, whereby a software driven computer system outputs a cyclic, or constant analog electrical potential to a reference electrode, in order to induce oxidation and reduction condition at a sensor electrode surface.

The present invention provides real time qualitative and qualitative analysis of neurotransmitter chemicals that are produced and utilized in a human or animal brain, or in other living tissue, such the tissue mass that is represented at 10 of FIG. 1c. The diffusion and metabolism of these chemicals is tracked in vivo or in vitro, and in real time, as the diffusion and metabolism of these chemicals occur in tissue mass 10. A visual CRT display 11 of the measurement results are provided for study in near real time.

FIG. 1a shows the complex construction and arrangement of a related prior art device. As can be seen, the prior art arrangements, of which this figure is an example, requires a large number of individual structural components, and even with this complexity all that the prior art does is to acquire raw data for much later use and study as the data is manipulation by the user. The present invention, as shown in FIG. 1b, provides a minimal number of structural components that operate to acquire data in real time, to automatically analyze the data, and then provide an analysis output to the user in near real time.

A detailed description of the system of FIG. 1a is provided in the publication *Monitoring Neuronal Activity—A practical Approach*, Edited by J. A. Stamford, Oxford University Press, copyright 1992, incorporated herein by reference for the purpose of indicating the background of the invention and illustrating the state of the art.

This invention consists of several hardware and software components.

1. As used herein, the phrase "computer" refers without limitation to a commercially available computer, for example, one having a high speed 32-bit CPU. The computer desirability includes a math processing unit, at least four megabytes random access memory, a VGA monitor (CRT), a keyboard, at least one expansion slot, and a hard disk having sufficient storage space for program and data storage. A Hewlett-Packard PCL-5 compatible laser printer, an Epson compatible dot matrix printer, or a Hewlett Packard compatible pen plotter to provide hard copy output is also desirable. An embodiment of the invention was developed on "DELL" computers with Intel 80386 and 80486 CPUs.

2. As used herein, the phrases "application software" and the "program" refer to a computer program running on the above mentioned computer to control the operation of the various aspects of this invention. In an embodiment of the invention, the application software was written in the "C' programming language and was compiled with the Intel 386/486 C Code Builder Kit.

3. As used herein, the phrase "I/O board" refers to a commercial data acquisition board that is compatible with the above-mentioned computer. The I/O board preferably has two 12-bit digital-to-analog converters, an analog-to-digital converter with 16 channels, and at least 16 digital-to-digital input/output ports. An embodiment of the invention used the Scientific Solutions, Inc. "Lab Master DMA" 12-bit I/O board and the Analogic Corp. MSDAS—16M 16-bit I/O board.

4. As used herein, the term "potentiostat" refers to any commercial or in-house constructed circuitry that is compatible with the above mentioned I/O board and computer. The potentiostat controls the application of potentials to the reference electrode and converts the resulting ambient sensor current signals into voltages that are read by an A/D convertor.

5. As used herein, the term "sensor" or "sensor electrode" refers to any device that detects the chemical oxidation and reduction of a neurotransmitter and is capable of conducting ambient sensor chemical signals to the potentiostat.

6. As used herein, the term computer system refers to the combination of items listed above.

The invention provides for several distinct modes of operation. As used herein, the term "mode" refers to the type of waveform that is generated by computer system 16 of FIG. 1c, nonlimiting examples of such modes are, Chronoamperometery, Fast Cyclic Voltammetery, and constant potential amperometry.

The square wave or Chronoamperometeric waveform of FIG. 8, is generated by switching the voltage that is applied to reference electrode 9 between two different values. As an example, the preferred method for the detection of dopamine may comprise pulsing electrode 9 between +0.55 volts and 0.0 volts.

Two other modes are triangle (FIG. 10) and "W" (FIG. 12), shaped waveforms or Fast Cyclic Voltammeteric waveforms. In the triangular waveform of FIG. 10, the voltage that is applied to reference electrode 9 is increased in a generally linear manner from −0.5 volts to +1.0 volts, and then decreased back to −0.5 volts. In the "W" waveform of FIG. 12, the voltage that is applied to reference electrode 9 is decreased from 0.0 to −1.0, increased from −1.0 to +1.0, decreased from +1.0 volts to −1.0 volts, then increased back to 0.0 volts to complete the waveform. The square, triangular and "W" waveforms are normally repeated every second, however the waveforms can be generated numerous times per second and averaged to improve the signal-to-noise ratio of the sensor signal readings.

In accordance with the invention, computer system 16 uses a menu-driven approach to guide the user through operation of the apparatus. The user is assisted in selecting parameters for the type of chemical detection and measurements to be taken. Default values are supplied by the application program for all necessary operating parameters that are not input by the user.

Figure 2A:
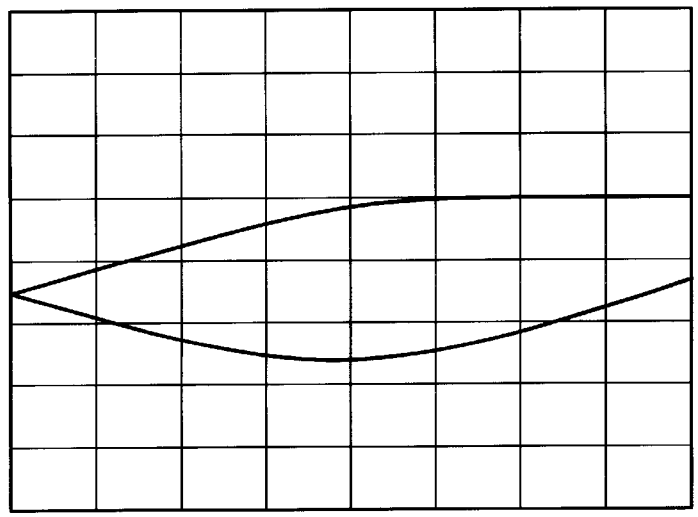
FIG. 2a shows the waveform output of an unsynchronized computer system of FIG. 1a, and FIG. 2b shows the waveform output of a correctly adjusted and synchronized computer system of FIG. 1c, as displayed on the CRT of FIG. 1c.
Figure 2B:
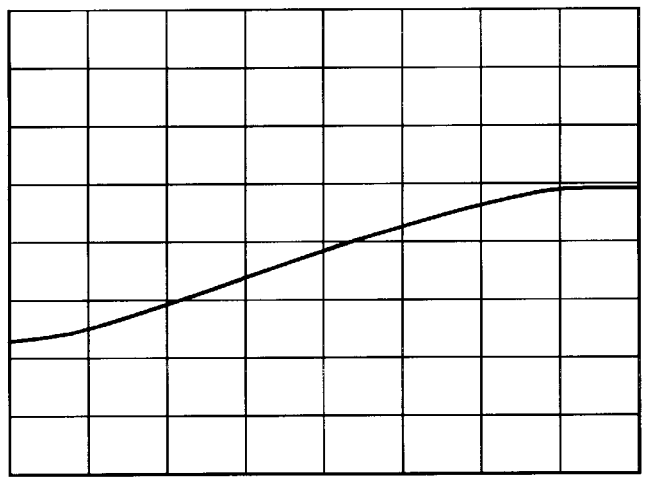

The invention is generally hardware independent, and is capable of working with a variety of commercial computers, I/O boards, potentiostats, reference electrodes and sensors. In each step of the process of electronically generating the reference electrode driving waveforms, and measurement of the resulting sensor signal, differences in the timing of the computer system may occur. For example, filters, if present in the potentiostat, cause delays in signal through-put, and different sensors usually have different capacitance values, resulting in a difference in sensor charging rates. If computer system 16 starts measuring the A/D signal that is provided by sensor 12 as soon as the D/A reference electrode driving voltage is generated and applied to the reference electrode, part of the A/D sensor signal usually will not be measured because of this delay. As a feature of the invention, in order to compensate for hardware differences, computer system 16 generates a fast cyclic voltammagram at a 500 volts per second scan rate. With a 10 Mohm resistor connected between the sensor port and the reference electrode port of potentiostat 28, the waveform appears in the oscilloscope screen on CRT 11 as a blue (oxidation) curve and white (reduction) curve. When the computer system timing matches the hardware delay correctly, the reduction curve will overlay the oxidation curve in a symmetrical manner, as is shown in FIG. 2b. When the sensor signal is delayed by the above mentioned hardware, these two curves do not overlay and will be asymmetrical in pattern, as in FIG. 2a. The user is CRT-prompted to adjust the timing of computer system 16 to match the time delay of the hardware by pushing the "left arrow" and "right arrow" keys on the computer system keyboard. Each keystroke changes the computer system timing by one microsecond, increasing or decreasing the computer system time delay until the curves are correctly symmetrical and overlaid as in FIG. 2b.

CALIBRATION PROCEDURE

As a feature of the invention, a procedure for calibrating sensors 12 to the chemical of interest is automated and is an integral part of computer system 16. There are a number of operating parameters that may be varied according to the type of measurements to be taken and according to the environment in which these measurements are recorded. Since the thermodynamics of sensors 12 vary not only between different types of sensors but also between sensors of the same type and construction, each individual sensor 12 must be calibrated and the calibration data stored and later recalled for use with that individual sensor only.

As used herein, a method for applying a waveform to the sensors refers to the way in which the waveforms of FIGS. 8, 10, 12, 15, and 16 are applied to sensor(s) 12 relative to reference electrode 9 in a one second epic. Nonlimiting examples are (1) delay method, or one waveform per second with a delay until the next second (see FIGS. 8, 10 and 12); (2) fast/slow method, or rapid pulsing with the average of the waveforms being recorded once per second; (3) real-time method, with the waveform being continuously sent to the sensors; and (4) subtraction method, where a reverse waveform is subtracted from the working waveform to remove background noise (see FIG. 15). Other examples of methods used to apply the waveforms to reference electrode 9 include frequency or amplitude modulated waveforms (see FIG. 16).

As used herein, "frequency" refers to the number of cycles per second a waveform is generated by computer system 16, whether or not the waveform is actually generated that number of times per second (i.e., a 5 Hz waveform can be generated five times per second, but in the delay method only 1 waveform of 200 millisecond duration is generated per second).

Figure 11:
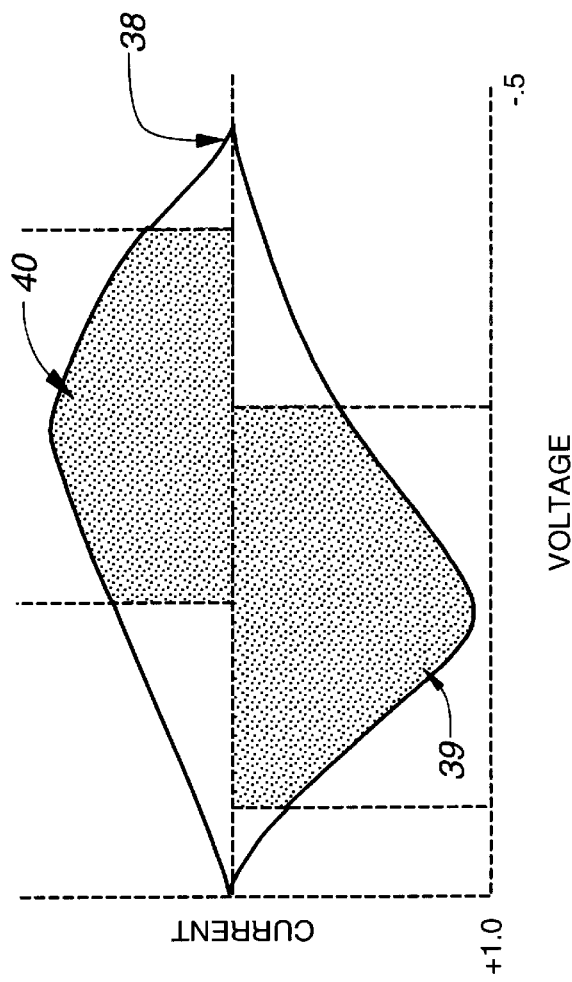
FIG. 11 shows an example of the A/D sensor signal that results from the applied electrical potential of FIG. 10, FIG. 11 also showing the preferred area of the A/D signal waveform to be sampled and integrated in order to measure the sensor's oxidative and reductive states.

As used herein, "scan rate" refers to the time interval that is required for the fast cyclic triangular and W-shaped waveforms of FIGS. 11 and 12 to complete one cycle, and in one embodiment of the invention, the scan rate is controlled by the voltage that is applied to an electrical integrator (i.e. 3 volts applied to the integrator results in a 300 volts per second scan rate).

Figure 10:
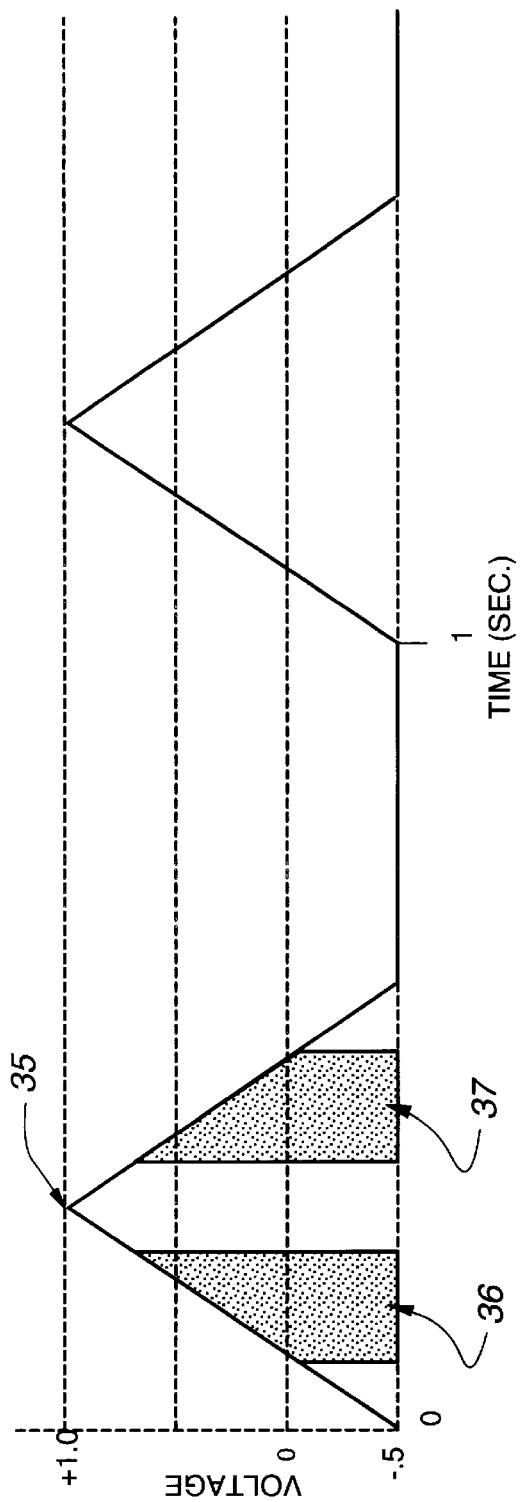
FIG. 10 shows a computer generated triangular cyclic voltammagram that is output by the D/A converter and the potentiostat to the reference electrode of FIG. 1c, wherein FIG. 10 also shows the corresponding areas of the triangular wave to be integrated by the apparatus of FIG. 1c.

As used herein, "integration range" refers to that portion of the sensor signal waveform that is actually used as representative of the response of a sensor(s) 12 to the chemical of interest, for example, see 36 and 37 of FIG. 10.

When using square wave chronoamperametry, it is preferred to exclude the initial non-Faradaic charging current as shown by 20 and 21 of FIG. 9. This procedure improves the signal-to-noise ratio of the sensor signal due to measuring a small signal on a small decaying or stable current, rather than measuring a small signal on a large charging current. A range of from 20% to 100% of the length of each portion of the waveform is used as a default value, see 20 and 21 of FIG. 9.

In triangular and W-shaped fast cyclic voltammetery, the portion of the sensor waveform to be integrated varies not only with the chemical being measured but also varies among sensors. In the preferred method of determining what portion of the waveform to measure, computer system 16 determines the background noise level of sensor(s) 12, and subtracts this background value from the raw sensor signal (compare FIG. 14 to FIG. 13). When sensor 12 is subjected to a small amount of the chemical of interest, the area of the signal response becomes visible in the oscilloscope window of graphical display 11, and the user then selects the specific voltage range to integrate, see 54 and 55 of FIG. 14. Calibration then proceeds as described below.

Operating parameters are established at the beginning of the calibration procedure (see Table 2), and are then automatically stored in a parameter file that is used by the sensor(s) 12 to be calibrated. The necessary operating parameters are, mode, method, frequency, applied and resting potential (for chronoamperametery) or scan rate (for fast, cyclic voltammetery), integration range, A/D channels or channel, and the increment size of the calibration chemical as expressed in micromolar increments.

Sensor 12 is placed in an artificial environment resembling the environment where actual measurement is to take place at a later time. As an example, for the in vivo detection of dopamine in the rat brain, the sensor is calibrated in a beaker containing PBS (Phosphate Buffered Saline). A Silver/Silver-Chloride (Ag/AgCl) reference electrode 9 is also placed in the beaker. Computer system 16 is activated to generate the preselected waveforms that are applied to reference electrode 9, and the raw sensor waveform is displayed in near real-time in both graphical (i.e. oscilloscope image) and numerical format. Oscilloscope window 11 displays an optimum waveform template for comparison to the actual waveform (in chronoamperametry mode only). At this time, the presence of a defective or cracked microsensor 12, or a weak reference electrode 9 is obvious to the user due to failure of the waveform to match the template or due to steadily increasing signal values.

When the sensor trace on screen 11 approximates the optimum waveform template, and has stabilized, the user prompts computer system 16 to record the sensor's background signal for later use. If a sensor 12 has been treated to enhance selectivity, it is next tested for selectivity to the chemical of interest over other chemicals which may be encountered. As in the previous example, this is accomplished by adding an increment of ascorbic acid similar to the concentration found in the rat brain to a beaker of PBS.

At the user's prompt, computer system 16 records the response of sensor 12 for later use. Equal increments of the chemical of interest are then added to the beaker, with computer system 16 recording the response of sensor 12 between each increment. The sum of all increments should cover the range that is expected to be detected in later use of the sensor (i.e., in a rat brain).

Figure 3A:
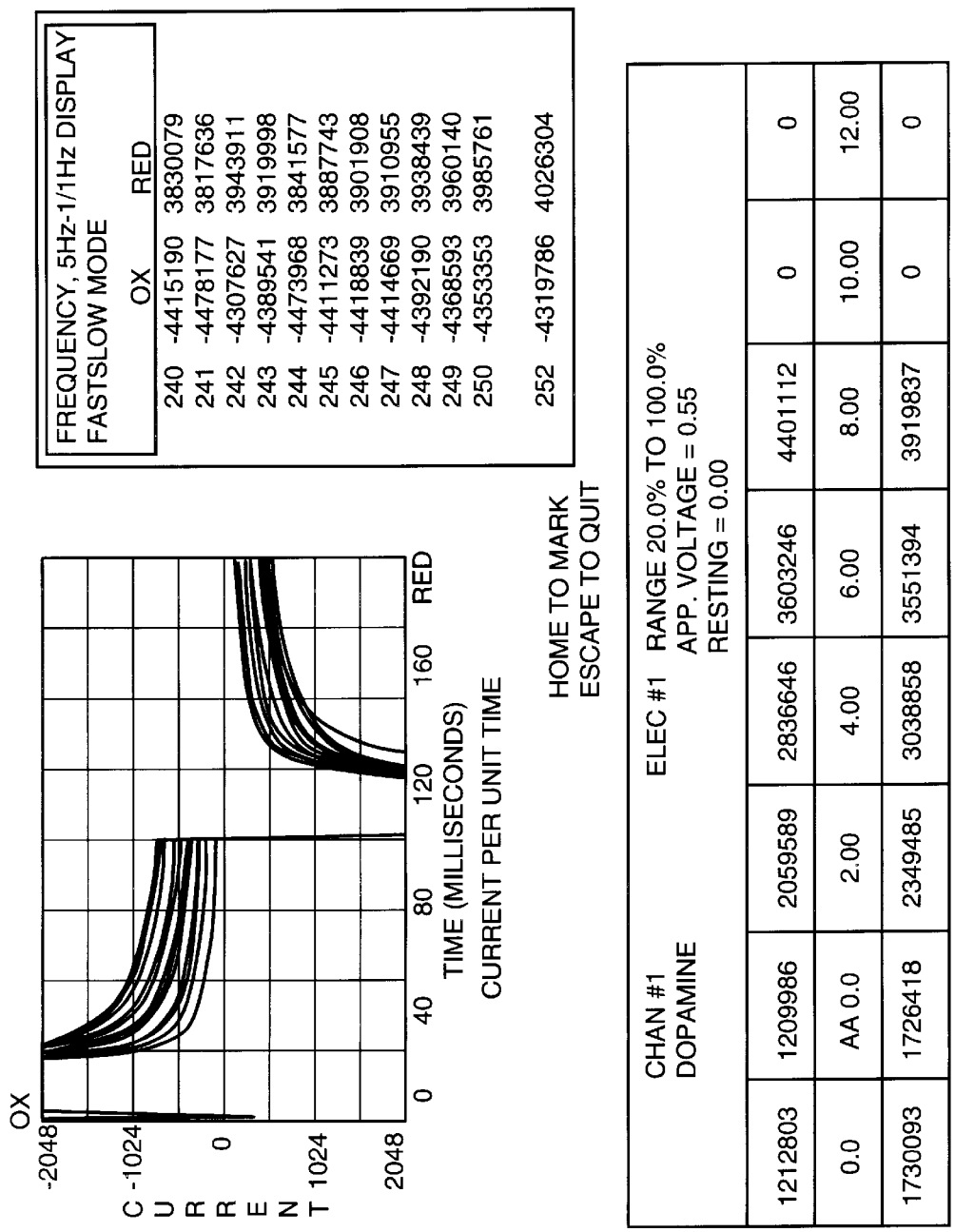
Figure 4:
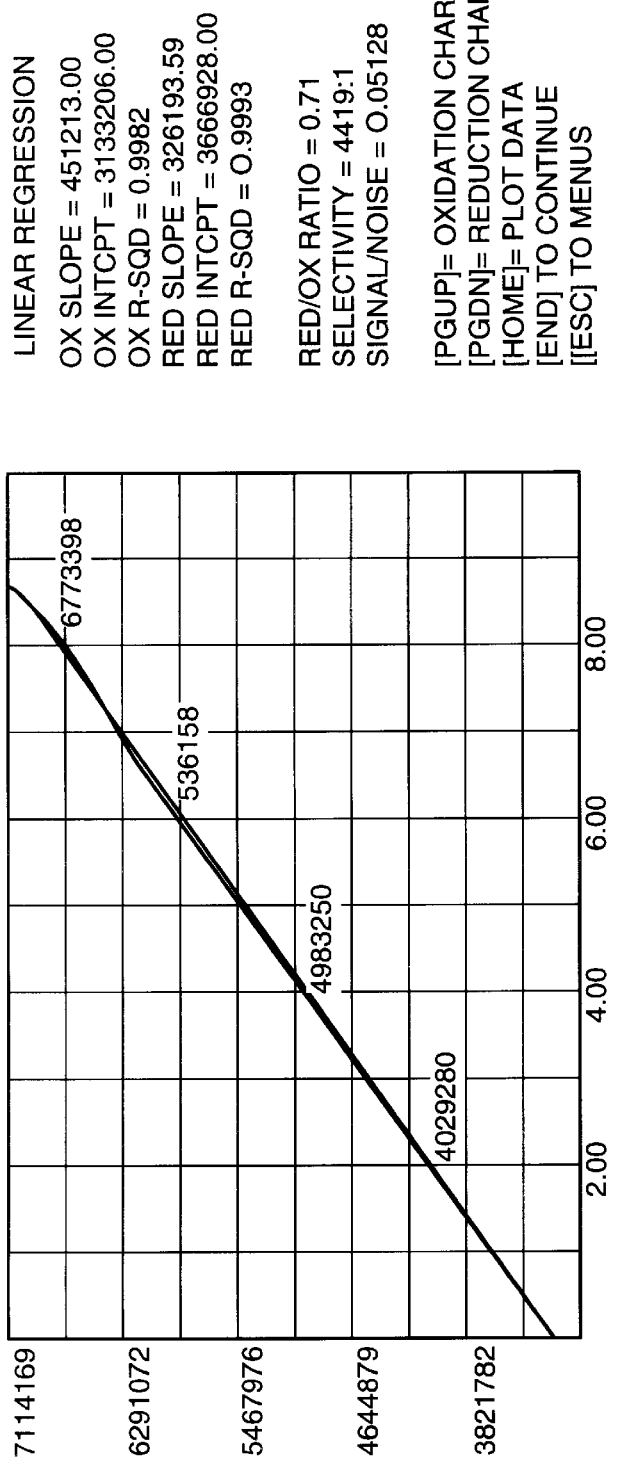
FIG. 4 shows linear regression data that is generated from the results of the chronoamperometry calibration shown in FIG. 3a, as displayed on the CRT of FIG. 1c.

An example completed chronoamperametery calibration is represented in FIG. 3a and a fast cyclic voltammetery calibration is represented in FIG. 3b, both of which are displayed on CRT 11. Computer system 16 then computes the suitability of sensor 12 for its intended purpose. This includes the display of linear regression data (see FIG. 4) in both graphical and numerical format, such as the slope of the oxidation and reduction curves, their intercepts, and their correlation coefficients. The correlation coefficients for both oxidation and reduction slopes should be at least 0.997, and sensors 12 with less linearity are recalibrated or rejected. The red/ox ratio, the selectivity of that sensor, and the signal-to-noise ratio for that sensor are also computed and displayed. FIG. 4 shows the linear regression as displayed on CRT 11 for the calibration completed in FIG. 3a. The computed data is printed or plotted on the attached printer output device 25 of FIG. 1c.

As used herein, "reduction/oxidation ratio" (see 905 of FIG. 25) refers to the ratio of the reduction slope to the oxidation slope for a sensor 12, and this ratio is an indication of the chemical that is being detected by the sensor.

As used herein, "signal-to-noise ratio" (see 903 of FIG. 25) refers to the smallest signal that can be reliably detected over and above the ambient sensor noise signal of the apparatus, and is expressed in micromolar concentration of the chemical of interest. The signal-to-noise ratio is calculated as three times the standard deviation of the baseline.

REAL TIME DATA ACQUISITION

As described above, and as a feature of the invention, prior to data acquisition with the apparatus of FIG. 1c sensor 12 is calibrated with the chemical of interest, and the calibration results or values are stored in system memory 32 and disk 125 of computer system 16 for later use. This calibration data is used by computer system 16 to transform the raw signal from sensor 12 into actual chemical concentrations which are then stored and displayed in near real time.

Figure 5:
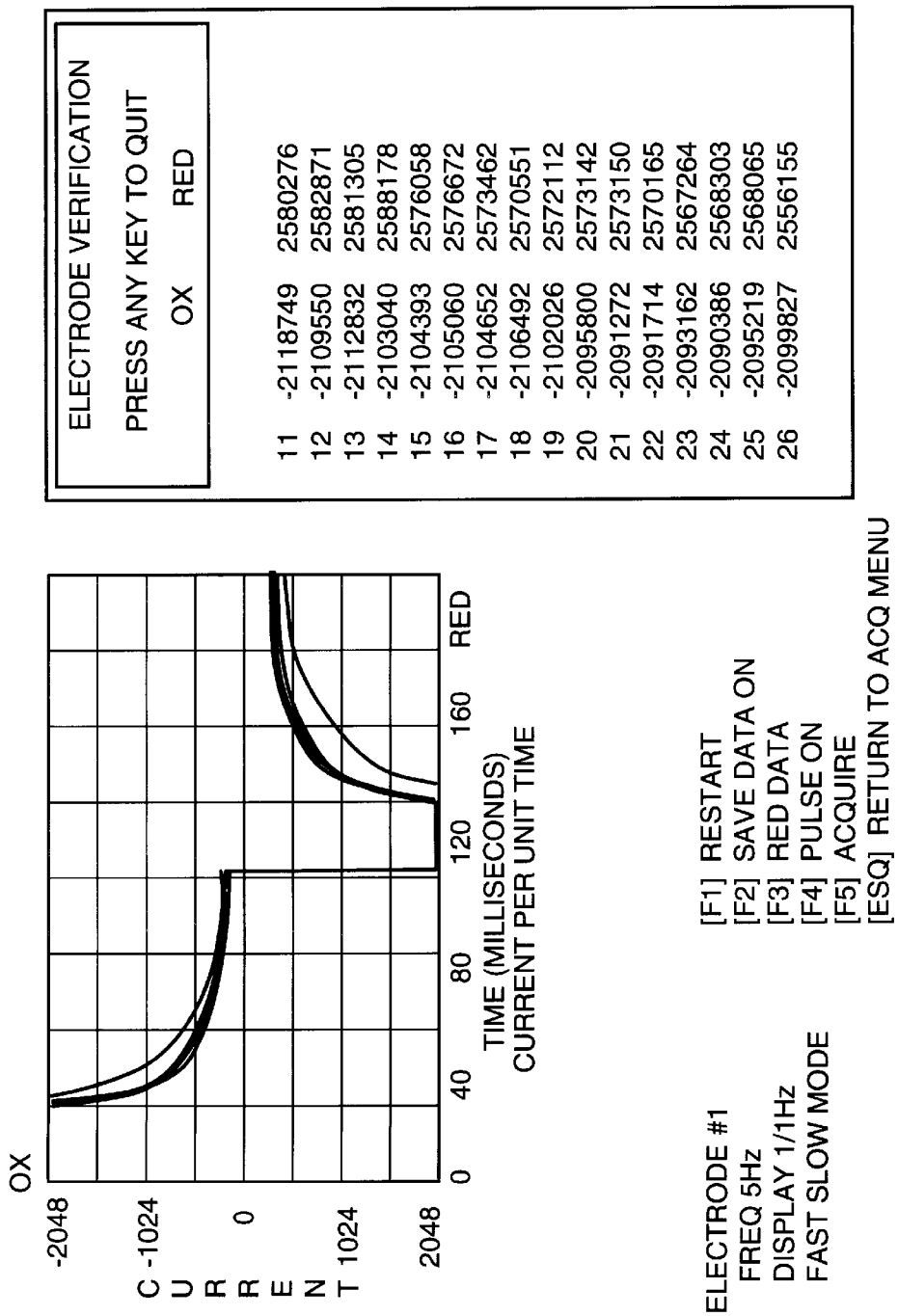
FIG. 5 shows how the integrity of the sensor electrode and baseline stability at the beginning of data acquisition is verified, as displayed on the CRT of FIG. 1c.

One or more previously-calibrated microsensor(s) 12, and a Ag/AgCl reference electrode 9 are placed in a selected area of tissue mass 10 in order to detect the chemical activity that occurs in very small areas of tissue 10. When computer system 16 is activated to start data acquisition, a data file is opened, and the sensor's calibration data is written to the header of this data file. An oscilloscope image of the selected waveform is then displayed, along with the numerical data representing the waveform, see FIG. 5. At this time, and after sensor(s) 12 has stabilized (i.e., after the sensor's output signal has stopped drifting, said drifting being caused by sensor(s) 12 coming in physical contact with electroactive chemicals released from ruptured cells) computer system 16 establishes an initial baseline for the data acquisition display.

Figure 6:
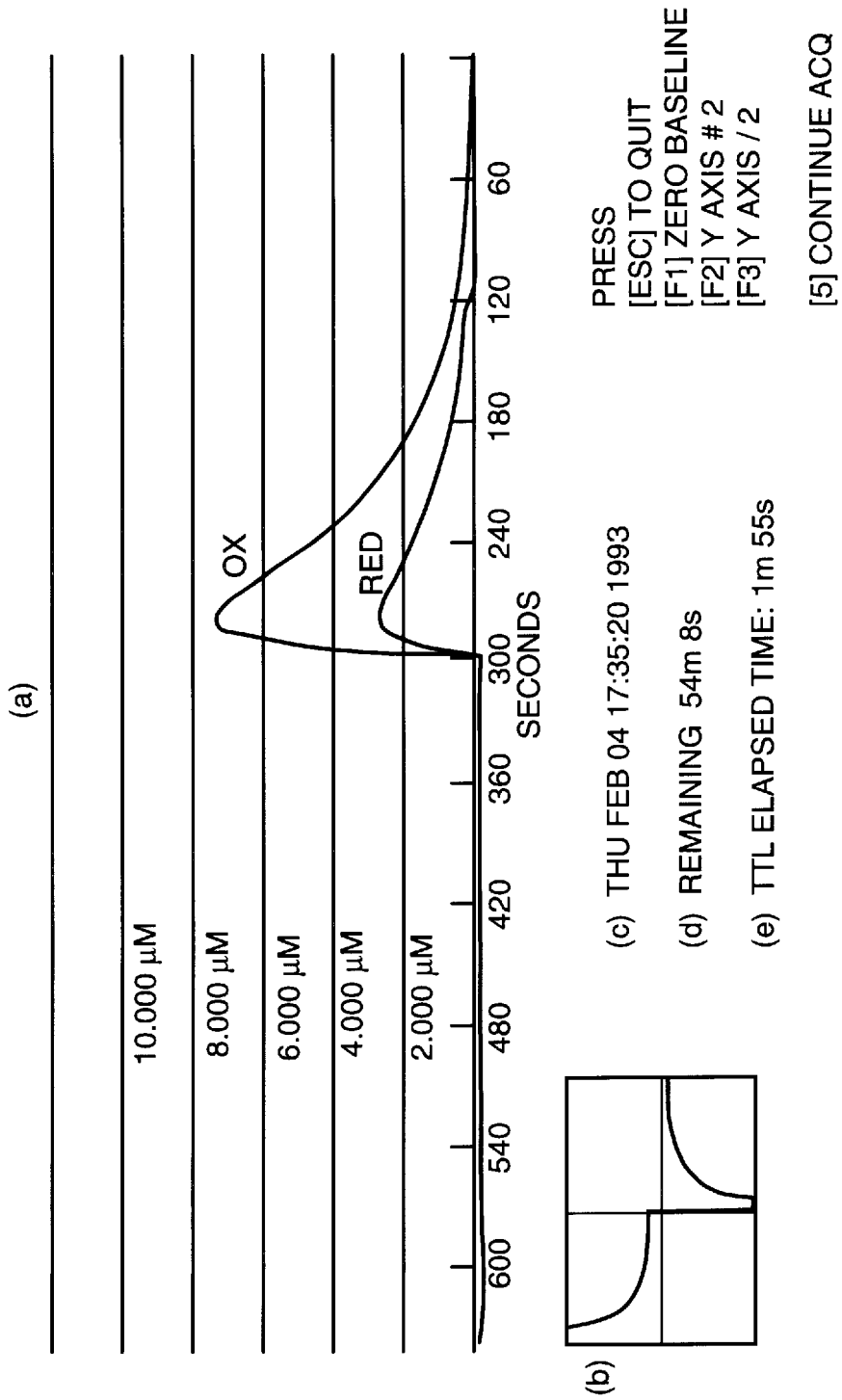
FIG. 6 is an example of the near real time graphical CRT display that is presented on the display of FIG. 1c, showing a time versus amplitude plot of an oxidation curve, a reduction curve, the raw waveform (b) at the sensor electrode surface, and timing features produced by operation of the apparatus of FIG. 1c.

If the waveform indicates that sensor(s) 12, after being placed in tissue 10, is still properly functioning, system 16 then presents, as in FIG. 6, (a) a graphical display of the real-time raw sensor data in near real-time expressed in actual micromolar concentration, (b) an oscilloscope image for monitoring the raw sensor signal waveform, (c) a real time clock with day, month, time, and year, (d) a count down run time clock which displays the time remaining in the current data file, and (e) an elapsed time indicator displaying time since the last external event was initiated.

The output signal from sensor(s) 12 is measured in real time, and the integrated sensor signal waveform value is stored in a data buffer and converted to an equivalent micromolar chemical concentration, and is scrolled across graphical display 11 in near real time. At this time, if an external apparatus is used to stimulate chemical production within tissue mass 10, or to inject the chemical of interest, TTL port 33 of I/O system 27 is activated. This activation places a marker in the current data file to mark the beginning of chemical activity. CRT color is used as a medium for differentiating between different displayed values (i.e., external events, positive data (above baseline), and negative data (below baseline)), in the data trace scrolling across graphical display 11.

During pauses in the acquisition of data, computer system 16 stores in the above-mentioned data file that was previously created the data that is currently held in data buffers in computer memory 32. The computer also displays information relative to the last series of data points collected, including maximum amplitude of the sensor signal, rate of decay of the signal, clearance rate of the chemical of interest, and total time of chemical activity. Computer system 16 utilizes large but limited data buffers to store the real time data. If more data collection is required, a new data file is opened. The data in the memory buffers and in the data file are stored in the form of the raw integrated sum of the sampling of the oxidation and reduction portions of each waveform that is applied to reference electrode 9 and the equivalent micromolar chemical concentration. Time in seconds and the state of ports 33 are also stored in the buffers and data files.

Figure 7:
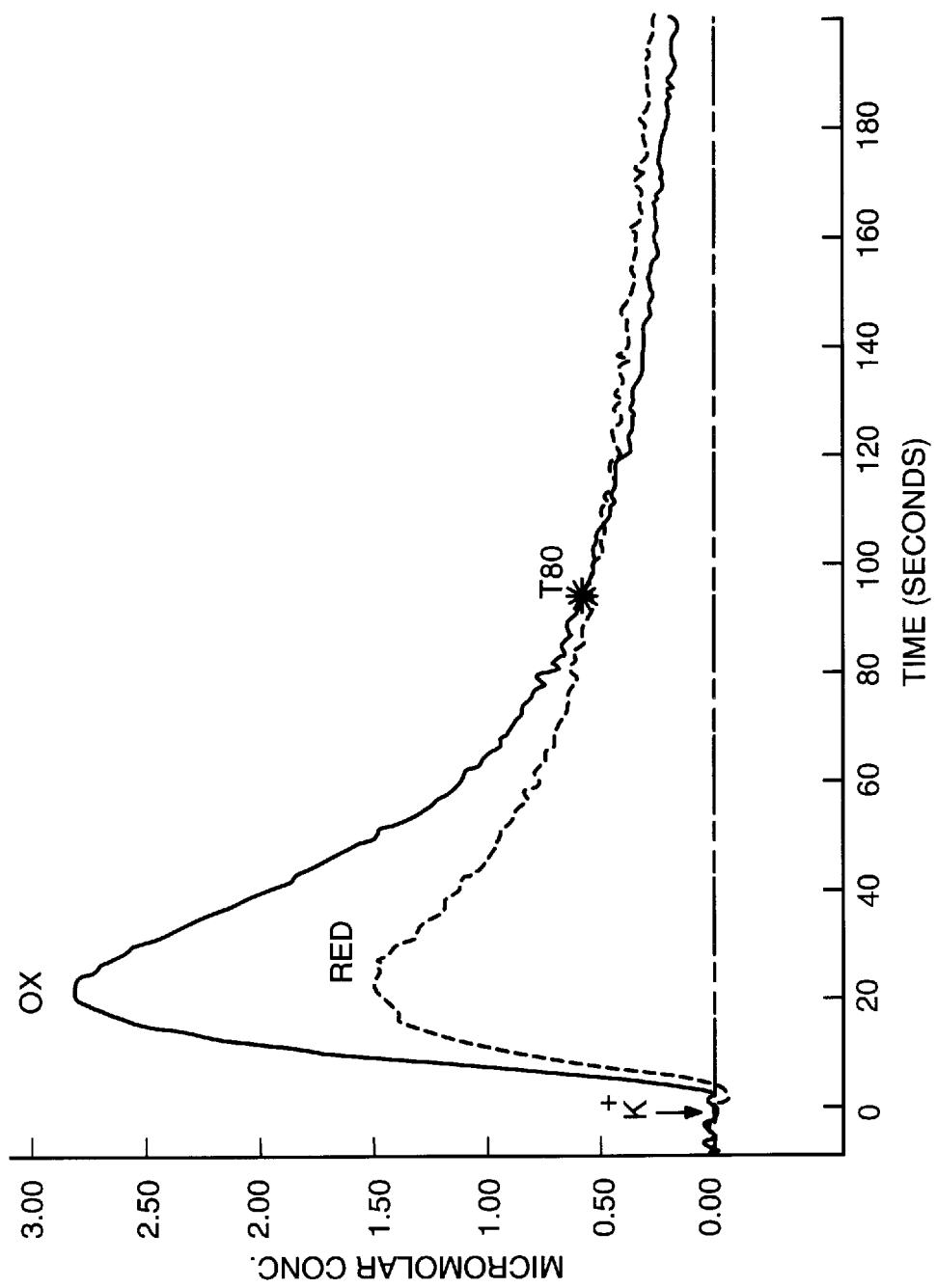
FIG. 7, including
Figure 7A:
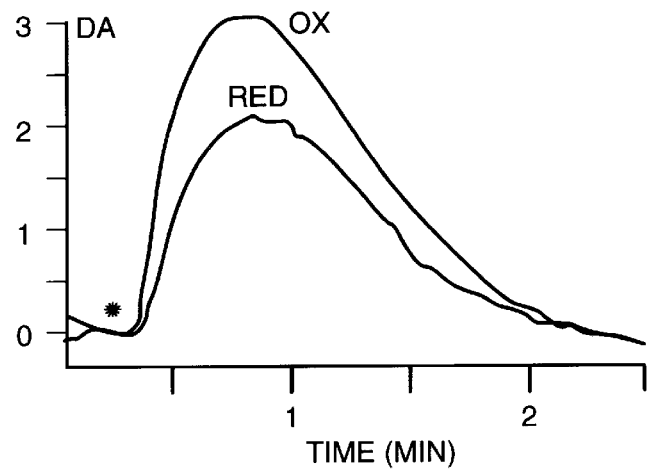
FIGS. 7a, 7b, 7c, shows the relationships between the oxidation and reduction curves, and how these curves are used to identify three specific chemicals, DA in FIG. 7a, 5-HT in FIG. 7b, and AA in FIG. 7c, as displayed on the CRT of FIG. 1c.
Figure 7B:
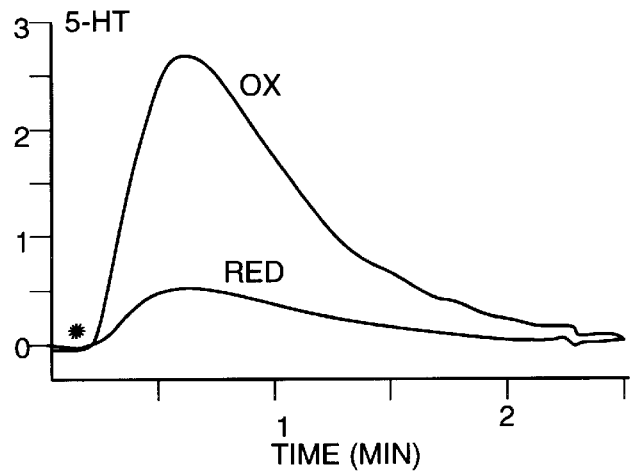
Figure 7C:
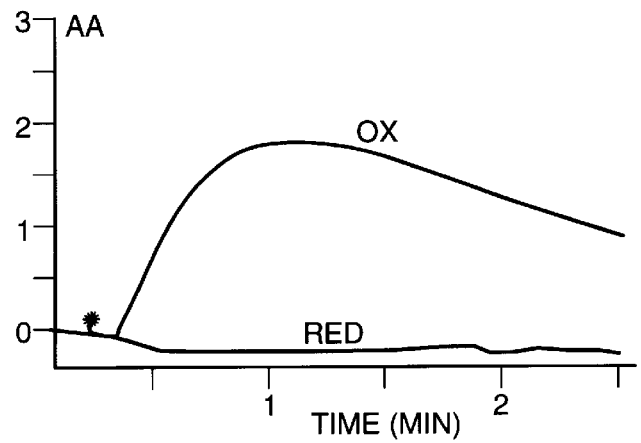

FIG. 7 demonstrates a typical graphical representation of a portion of a data file. K+ represents the point in time at which potassium is injected into tissue 10 to invoke a release of dopamine from the neurons that are next to sensor 12. OX is the oxidation response of sensor 12 to this injection of potassium, and RED is the reduction response, the red/ox ratio is approximately 0.50. FIGS. 7a, 7b, 7c show typical red/ox ratios for three electroactive neurotransmitters—DA, 5-HT and AA, demonstrating how differences in the red/ox ratio are used to identify the particular neurotransmitter substance that is being detected.

CHRONOAMPEROMETERIC WAVEFORM

For chronoampometry, the square wave electrical potential of FIG. 8 is applied to sensor 12 by way of reference electrode 9, to first induce an oxidation condition at the solution-to-sensor interface during the portion 14 of the waveform, and to thereafter induce a reduction condition at this interface during portion 15 of the waveform. To generate waveform 14 a negative electrical voltage is applied to reference electrode 9 to create the positive electrical potential 14 at sensor(s) 12. In accordance with a feature of the invention, the FIG. 8 square wave has a frequency in the range of about 5 to about 100 Hz. Square wave potential 14,15 finds utility with sensor electrodes ranging from a very small 8–10 micron diameter to a larger 30 micron diameter, and to integrated circuit sensors. An example of the use of such sensors 12 is in a brain region or space having multiple cells.

FIG. 9 shows an example of sensor output signal 30 that results from the applied electrical potential of FIG. 8 as generated through computer system 16 by the application software. Chemical activity at the surface of sensor 12 during both oxidation condition 14 and reduction condition 15 of the applied potential is gathered by computer system 16. More specifically, chemical oxidation data is gathered during time interval 20 of signal 30, as by computer integration of this portion of the FIG. 9 signal, and chemical reduction data is gathered during time interval 21 of signal 30, again by computer integration of this portion of the FIG. 9 signal. In accordance with a feature of the invention, integration of portions 20 and 21 is accomplished by high speed sampling of the FIG. 9 waveform at the rate of about 50 to about 200 Khz.

Sensor 12 is connected to potentiostat 28, which is in turn connected to A/D components 31 of computer system 16. The data that is collected at the surface of sensor 12 is stored in computer memory 32 and displayed on CRT 11 in near real time. The data can also be output to printer 25, to a plotter, or to disk storage 125 for later analysis.

Voltage 14,15 of FIG. 8 is applied to reference electrode 9 by way of computer system 16, I/O equipment 27, D/A converter 26, and potentiostat 28.

Signal 30 of FIG. 9 is provided to computer system 16 by way of sensor 12, potentiostat 28, A/D converter 31, and I/O equipment 27. Computer system 16 operates to read signal 30 at a very rapid rate, typically at rates from about 50 to about 200 Khz. While integration of portions 20, 21 of sensor signal 30 is preferred, which portions exclude the initial non-Faradaic charging portion of the signal, the operator may integrate any portion of the signal as is desired.

FAST CYCLIC VOLTAMMETERIC WAVEFORMS

As a feature of the invention, the triangular and "W" waveforms are generated by computer system 16 very much as the square waveform is generated; i.e., by locking on specific potentials for specific lengths of time. However, in one embodiment of the invention, a specific preselected voltage was applied to an electrical integrator embodied within potentiostat 28 to form the smooth slope of the triangle and "W" waveform. In another embodiment of the invention, I/O hardware 27 was capable of outputting preprogrammed waveforms such as sine waves, triangles, "W"s, and frequency or amplitude modulated signals.

FIG. 10 shows a triangular wave example of a cyclic potential 35 that is applied to reference electrode 9 of FIG. 1c by way of I/O 27, D/A converter 26 and potentiostat 28. Waveform 35 is shown as varying between −0.5 volt and +1.0 volt, the rate and the voltage range at which potential 35 is applied between these two points is variable and is software controlled in accordance with the invention. Triangular waveform 35 finds primary utility when sensor 12 is of small diameter, 30 microns or less and of shorter length, 100 microns or less. Triangular waveform 35 is normally used with the same methods of operation as the chronoamperometeric waveforms.

FIG. 10 also shows the preferred integration range of the oxidation portion 36 of triangle waveform 35 and the preferred integration range of the reduction portion 37 of triangular waveform 35. As with square waveform 14,15 of FIG. 9, triangular waveform 15 is software controlled and is selected by the user.

FIG. 11 shows an example of the sensor's output signal 38 that results from the applied triangular potential 35 of FIG. 10, this signal being applied by way of potentiostat 28, A/D converter 31, and I/O equipment 27 to computer system 16. The preferred integration ranges for oxidation portion 39 and reduction portion 40 of waveform 35 are also shown in FIG. 11. The areas 39,40 of waveform 38 to integrate varies with the neurotransmitter being measured, this difference in area being a characteristic of the chemical being measured.

FIG. 12 shows a "W" shaped waveform example of a cyclic electrical potential 46 that is applied to reference electrode 9 of FIG. 1c by way of I/O 27, D/A converter 26, and potentiostat 28. The triangular portion 41 of waveform 46 is shown as varying between −1.0 volt and +1.0 volt and −1.0 volt, the rate at which potential 46 is applied between the points −1.0/+1.0 and +1.0/−1.0 is variable and is software controlled in accordance with the invention. The method of generating waveform 46 is the same as the method of generating chronoamperometeric waveforms.

FIG. 13 shows an example of the sensor's output signal 49 that results from the applied triangular potential 46 of FIG. 12. This output signal is applied to computer system 16 by way of potentiostat 28, A/D converter 31, and I/O equipment 27. The preferred integration ranges for oxidation 47 and reduction 48 of waveform 46 are also shown in FIG. 13. In FIG. 14, signal 53 is the same as signal 49 of FIG. 13, except that the background noise of signal 49 has been subtracted by computer system 16. Signal 53 now more clearly shows the sensor's response to the addition of the chemical of interest to tissue mass 10. The area 54,55 of waveform 53 to be integrated varies with the neurotransmitter being measured, and this difference in area is a characteristic of the chemical being measured. Computer system 16 uses this type of background subtraction on both the triangle and "W" waveforms.

The initial reduction ramp 44 and the following oxidation ramp 45 of waveform 46 of FIG. 12 are used to strip away unwanted chemical residues from the surface of sensor 12, and ramps 44,45 are not integrated or used in the identification of specific chemicals. An example of the use of "W" shaped waveform 46 is when sensor 12 is used in the presence of neurotransmitters such as serotonin that tend to adhere to the sensor's exterior surface.

Figure 15:
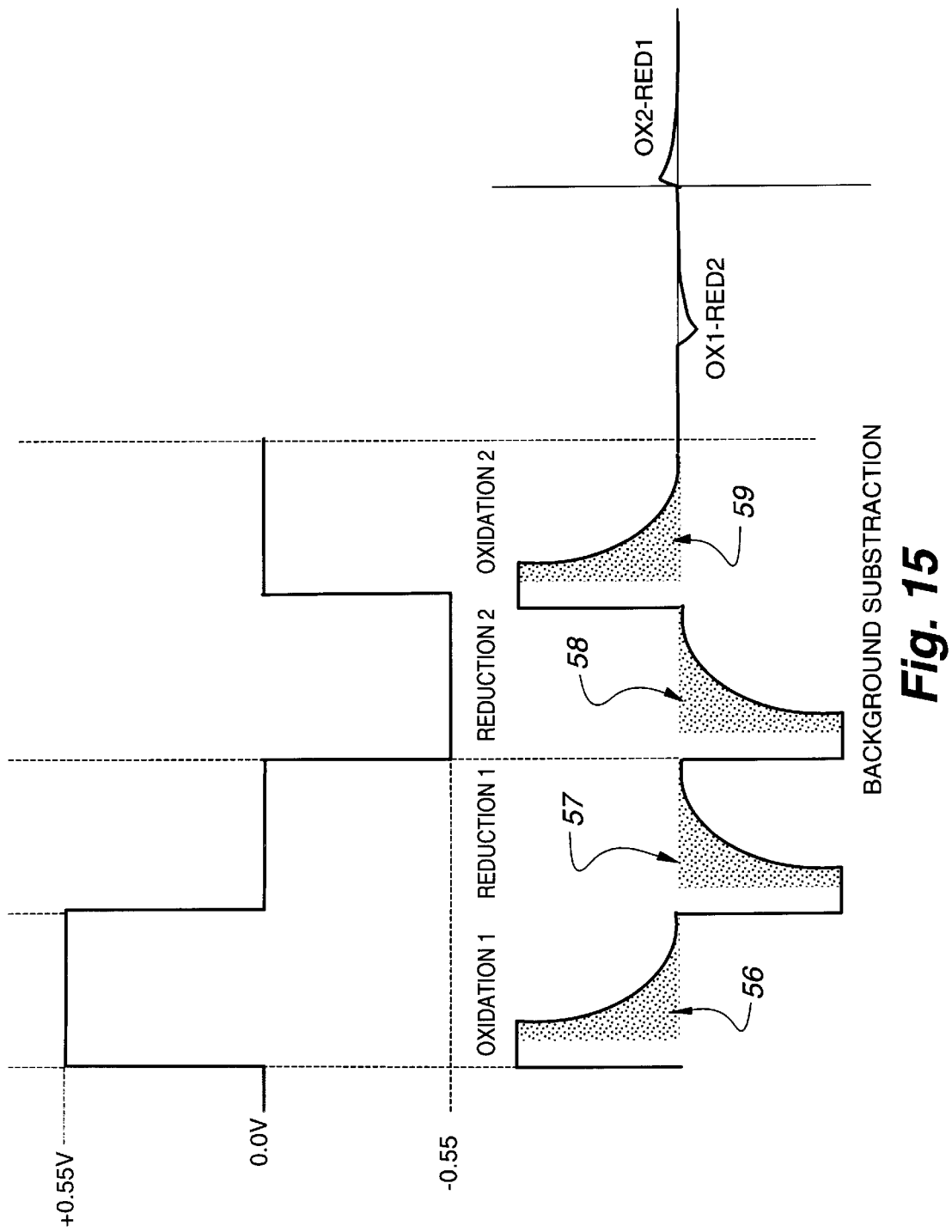
FIG. 15 shows first applying a computer generated square or positive polarity waveform, and then applying a reverse polarity of the square waveform, to the reference electrode of FIG. 1c, the displayed difference between the two sensor signal waveforms that result therefrom being the true response of the sensor to the chemical of interest.
Figure 16:
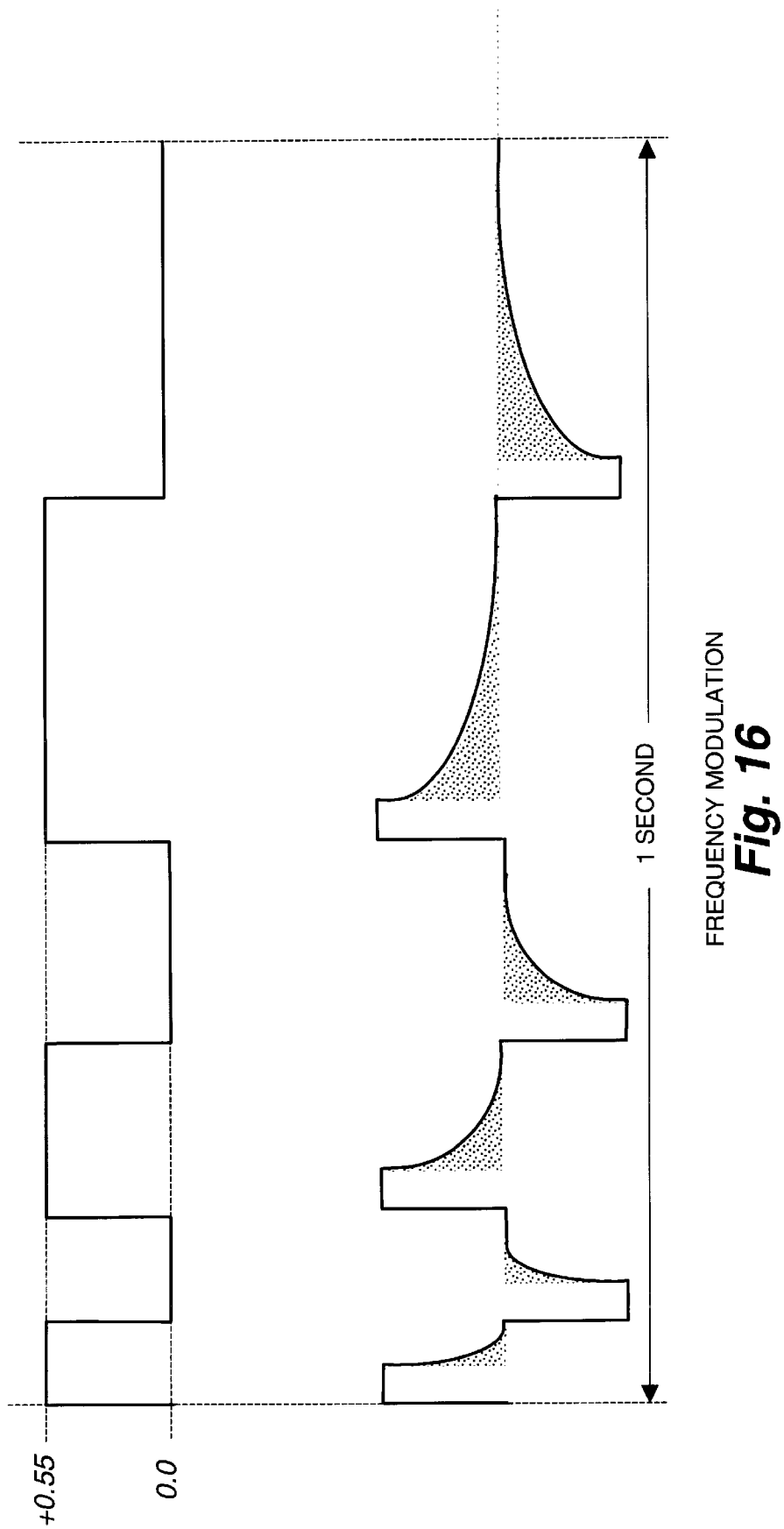
FIG. 16 shows applying the waveform of FIG. 15 at different frequencies, the rate of oxidation and reduction of electroactive molecules then being a further indication of the chemical that is being measured.

As a feature of the invention, the selected one of the three FIG. 8, 10, 12 waveforms that is in use at any given time is applied to reference electrode 9, and thereby to sensor 12, at a number of different frequencies and amplitudes. The waveforms may be pulsed once per second, may be pulsed numerous times per second and averaged for each one second epic, or may be pulsed continuously. As a feature of the invention, the operator has a wide range of options to use when measuring any of a wide variety of electroactive chemicals. For example, sensor 12 may be activated by computer system 16 to measure background noise as well as the actual response to the chemical of interest, and then subtract the background noise from the actual response, so that only the actual response is recorded and displayed. In addition, the frequency and the amplitude of the waveforms may be modulated in order to measure different aspects of the chemicals of interest. As an example, FIG. 15 shows subtracting the background noise that is measured in Reduction 1/signal portion 57 and in Oxidation 1/signal portion 56 from Oxidation 2/signal portion 59 and Reduction 2/signal portion 58, respectively, in order to record and display only the true response Ox1-Red2 and Ox2-Red1 of sensor 12 to the chemical of interest.

DIGITAL INPUT/OUTPUT

As a feature of the invention, computer system 16 of FIG. 1c interfaces to the outside world through TTL (transistor-transistor-logic) port 33 of I/O system 27. This construction allows computer system 16 to synchronize external events with the real time chemical detection. As a nonlimiting example, an electrical stimulator 200 of FIG. 1c may be connected to computer system 16, so that the time of stimulation may be correlated to a change in chemical activity.

DATA ANALYSIS AND EDITING

Figure 17:
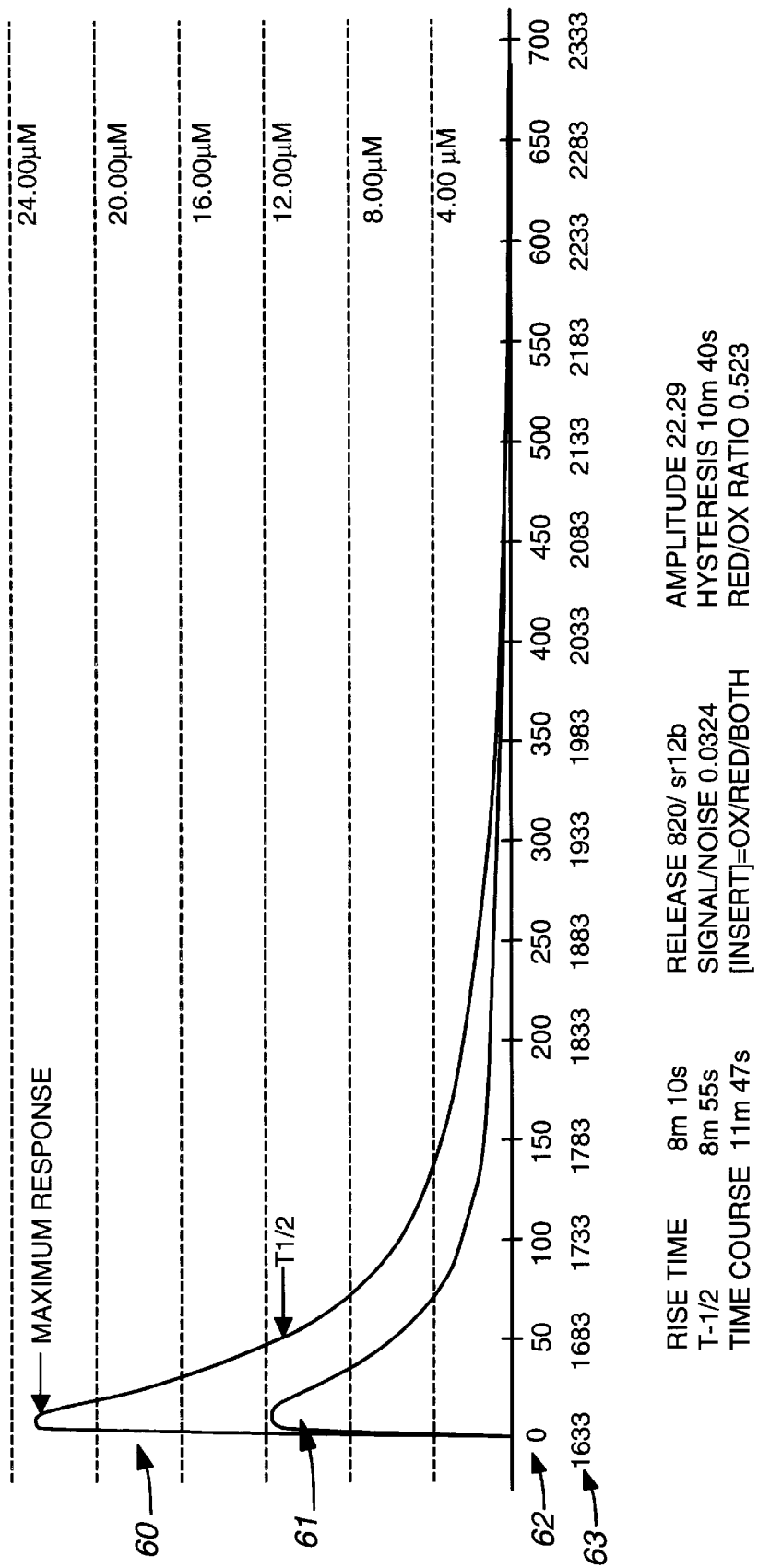
FIG. 17 shows an example of an automated graphical analysis of the response of a sensor to chemical activity, as automatically displayed on the CRT of FIG. 1c.
Figure 18:
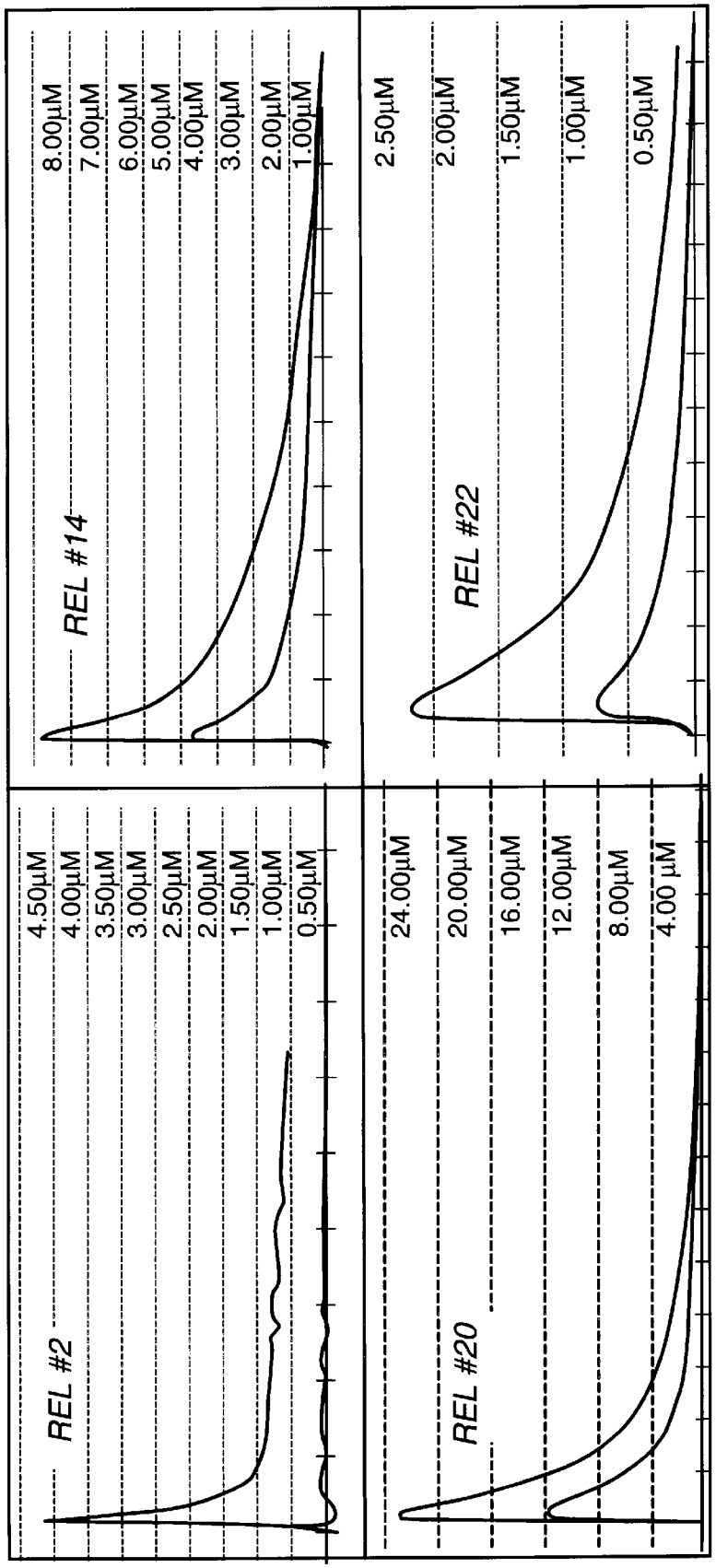
FIG. 18 shows an example of four sets of chemical data displayed simultaneously on the CRT of FIG. 1c.

As a feature of the invention, computer system 16 provides for automated analysis and editing of the sensed data files. This feature of the invention is used to examine and modify data files, and to obtain hard copy output of recorded events. This menu-driven feature of the invention loads a selected data file and guides the user to find and display significant chemical activity within the data file. The data is displayed on CRT 11 of FIG. 1c, either graphical as shown in FIGS. 17 and 18, or in tabular format, as shown in FIG. 25. In order to aid the user in understanding the data collected, computer system 16 automatically calculates a number of parameters relative to the data. The user has the option of viewing the entire data file, or of having computer system 16 select areas of the data file that meet the criteria of detected chemical activity. FIGS. 17 and 18 show typical in vivo sensor responses to the detection of Dopamine. Data curve 60 of FIG. 17, which is the oxidation response, is displayed in micromolar concentration on the y-axis, and in time in seconds on the x-axis. The corresponding reduction curve 61 is shown relative to oxidation curve 60. The upper set 62 of x-axis numbers is a display of the time duration in seconds of the chemical response. The lower set 63 of x-axis numbers is a display of the time duration in seconds since the beginning of the data file. The release number is also displayed along with some of the analytical results.

Figure 19:
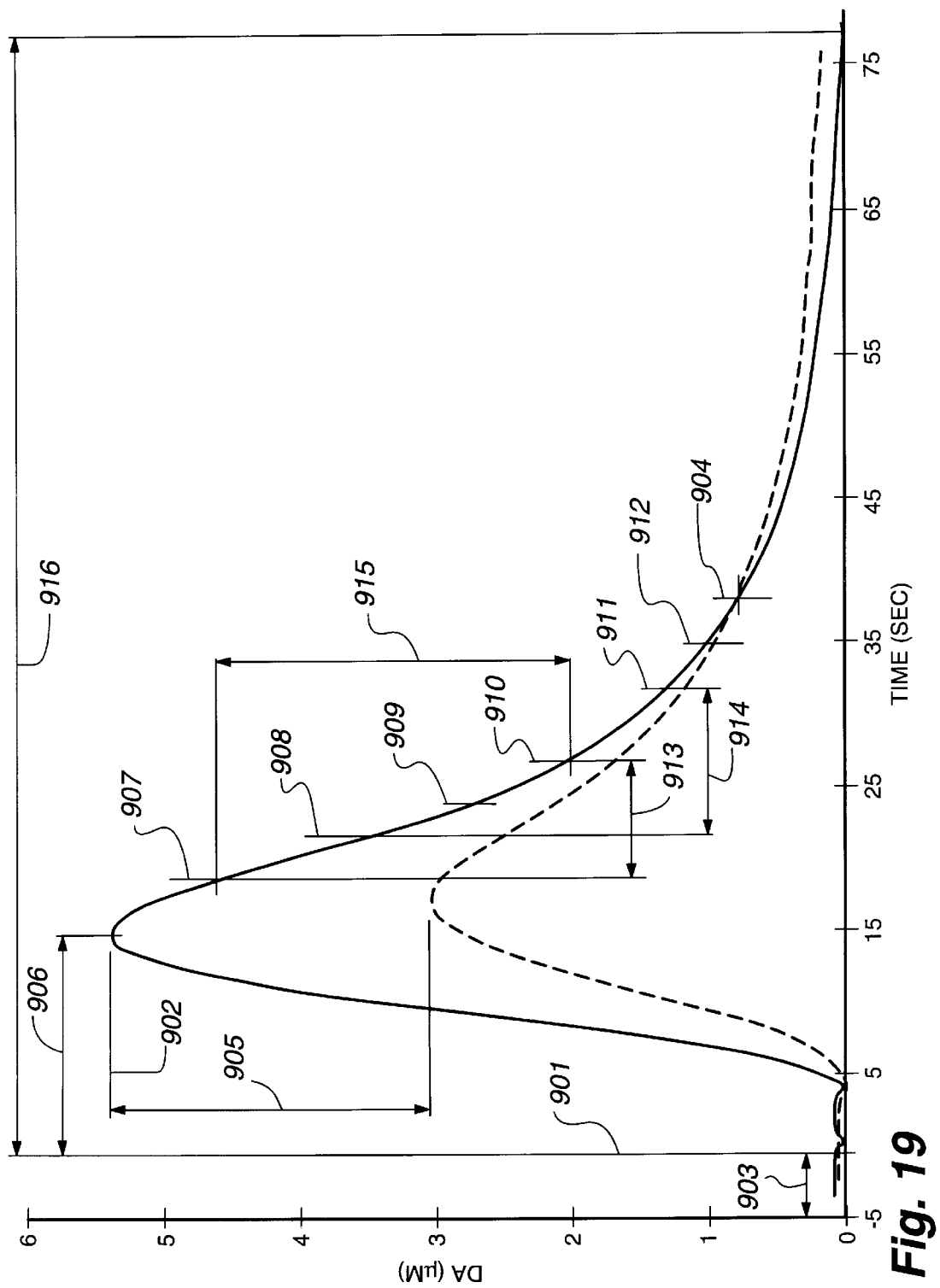
FIG. 19 shows exemplary oxidation and reduction curves, similar to FIG. 6, as provided in real time by operation of the apparatus of FIG. 1c.

FIG. 25 results from the data depicted in FIG. 19. Stated in another way, FIG. 25 shows data that is computed by computer system 16 for a typical response to the detection of an electroactive substance as displayed graphically in FIGS. 17 and 18. In FIG. 25, and in FIG. 19, RELEASE NUMBER 901 refers to the position of this response in relation to the entire data file. In this example, this chemical activity is the twentieth of thirty-seven detected by computer system 16 in this data file. AMPLITUDE 902 refers to the maximum increase in sensor response above baseline and is expressed as micromolar concentration. The baseline for each response is defined as the average of five data points prior to the TTL 33 marker. HYSTERESIS 904 refers to the time of intersection of the two data curves of FIG. 19, this being indicative of the end of chemical activity when both oxidation and reduction responses have normalized. RISE TIME 906 refers to the time in seconds from the initial response, or stimulation resulting in the response, to the time of maximum amplitude. The times T20, T40, T50, T60, T80, T90 (see 907, 908, 909, 910, 911, 912 of FIG. 25) refer to the time in seconds from maximum amplitude to that point where the response has decayed to 20%, 40%, 50%, 60%, 80%, and 90% of the maximum amplitude. T20–60 and T40–80 (see 913 and 914 of FIG. 25) refer to the time it took for the sensor output signal to decay between 20% and 60% and between 40% and 80% of the maximum amplitude, and are an estimate of the clearance time of the chemical of interest. Tc (915 of FIG. 25) is the rate of clearance of the chemical, and is a calculation of the slope from 20% to 60% of decay, expressed in micromolar concentration per second. TIME COURSE 916 refers to the total amount of time from the beginning of the event to the point where the sensor output signal returns to baseline. RED/OX RATIO 905 is the ratio of the reduction current to oxidation current response of sensor 12, and is an indication of the molecule or compound that was measured by the sensor.

The user has the option at any time while using the analysis portion of the program to printout the data in graphical or tabular form on output device 25 of FIG. 1c.

An editing feature of the invention allows for viewing and modifying the data files. The files may be viewed in whole, or only selected regions of the data file may be viewed on CRT 11. Event markers may be added or removed, as well as aberrant data points. Raw data can be extracted from the overall file and stored in separate files for analysis by commercial graphing and plotting software. After editing the data file, the user has the option of restoring the file and returning to the Analysis portion of the invention and re-evaluating the data. Computer system 16 will not allow the user to change the original raw data file, edited data files must be stored with a different file name, thus preserving the original data for future analysis and editing.

Figure 20:
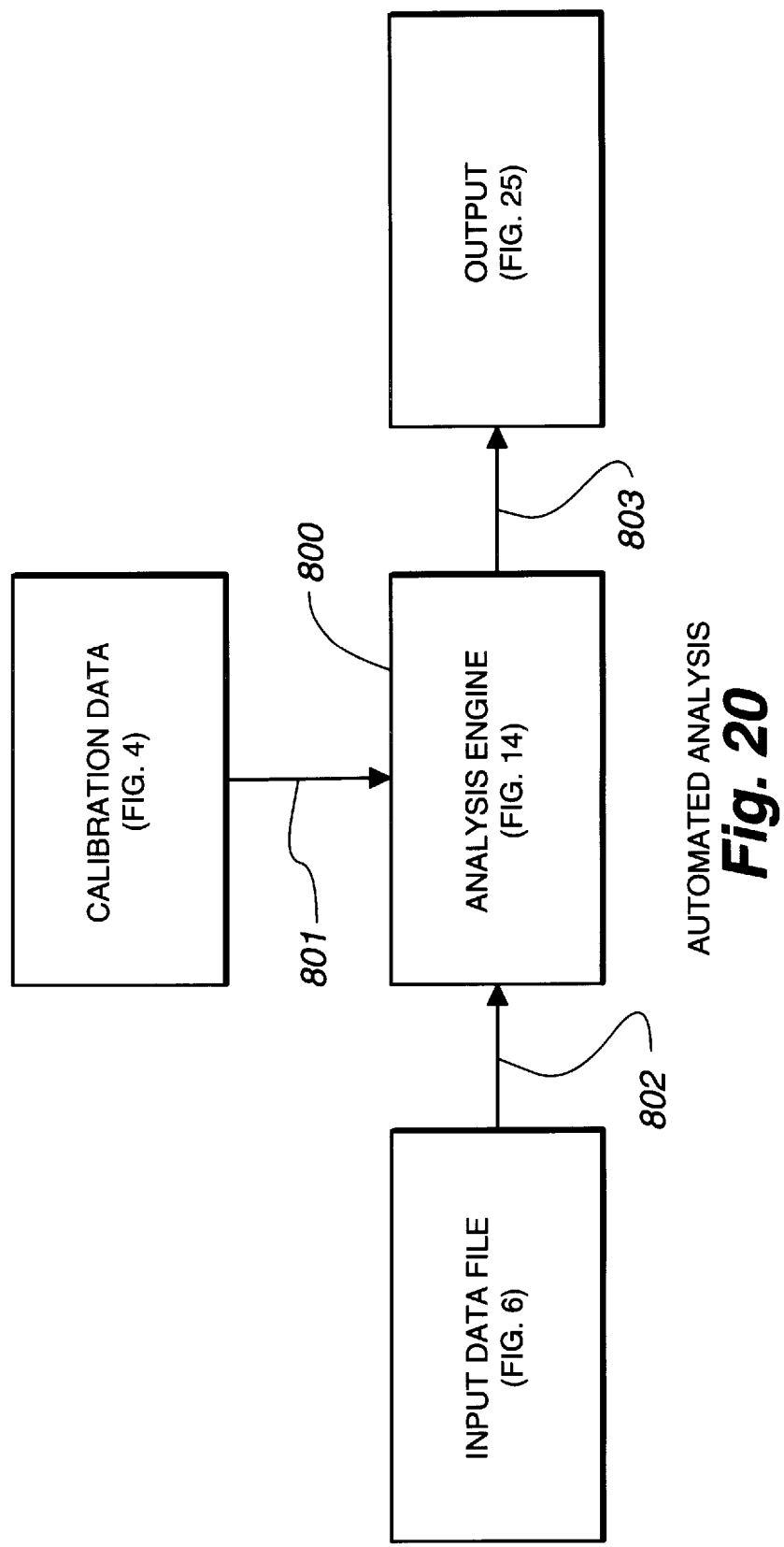
FIG. 20 is another showing of the present invention whereby an automated analysis engine is provided with input from the calibration data of FIG. 4, and from an input data file that is represented by the oxidation/reduction curves of FIG. 19, in order to enable the analysis engine to automatically provide an analysis output to the user in near real time, such an output being as is shown in FIG. 25.

FIG. 20 is another showing of the present invention whereby an automated analysis engine 800 is provided with input 801 from the calibration data of FIG. 4 and an input 802 from an input data file that is represented by the oxidation/reduction curves of FIG. 19, in order to enable analysis engine 800 to automatically provide an analysis output 803 to the user in near real time, such an output being as is shown in FIG. 25.

As stated previously, calibration data 801 of FIG. 20 is for a selected sensor 12, and this data carries information relative to the response of this unique sensor to known concentrations of a chemical of that is of interest. When this unique sensor is now used, as above described, in order to generate the FIG. 19 response of that particular sensor to the chemical of interest, as this chemical exists within tissue 10 as a result of the voltage applied to reference electrode 9, the present invention operates as analysis engine 800 in order to compare input 801 to input 802, and then automatically provide output 803, this output 803 providing the various analysis factors 901–916 that are shown in FIG 25.

Figure 21:
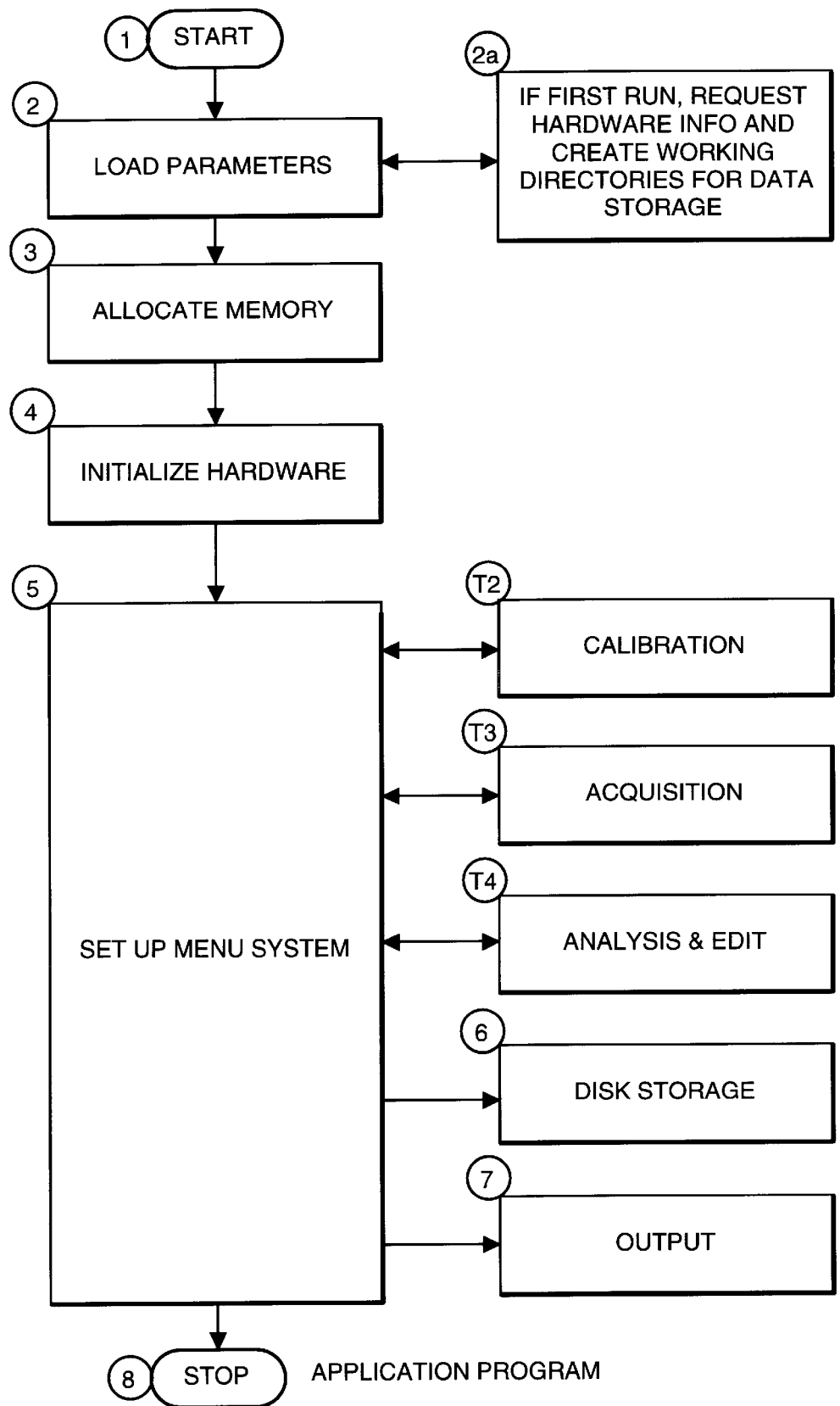
FIG. 21 is a flowchart of the application software portion of the computer system of FIG. 1c.

The following is an outline of the Application Program as presented in flowchart form in FIG. 21:

1. Start computer system.
   a. check hardware configuration for:
   1. graphics monitor
   2. sufficient memory to run progam and store data
   3. math processing unit
   4. type of hardcopy device, serial or parallel port.
2. Load parameters.
   a. if first time user, create a default parameter file (file #1).
   1. request hardware information from user.
   2. create necessary working directories on hard disk drive.
   b. If not first time user load parameter file #1.
3. Allocate memory for required memory buffers.
4. Initialize the I/O system and potentiostat.
5. Set up Menu system.
   a. Calibration procedure, see FIG. 22.
   b. Data acquisition, see FIG. 23.
   c. Analysis and Editing, See FIG. 24.
6. Disk storage.
   a. Store data files in data directory.
   b. Store updated parameter files in working directory.
7. Hardcopy output, of graphical or tabulated data.
8. Stop computer system.
   a. Close all open files.
   b. Reset hardware.
   c. Exit to operating system.

The following is an outline of the Calibration process set forth in flowchart form in FIG. 22.

1. Specify operating parameters.
   a. select blank calibration data file for this sensor.
   b. select waveform mode and method.
   c. select frequency.
   d. select oxidizing and reducing voltage potentials or scan rate.
   e. select integration ranges.
   f. input micromolar concentration of calibration increments.
   g. specify hardware for hard copy output.
2. Visual sensor check.
   a. configure system hardware as specified in step of FIG. 21.
   b. initiate hardware I/O system and potentiostat to start system.
   c. check for leaking or broken sensors.
   d. determine gain settings for each sensor.
   e. determine suitability for use as a chronomperometery or fast cyclic voltammetery sensor.
3. Add Ascorbic acid to determine sensitivity of this sensor to this chemical.
4. Add equal pre-determined volumes of the chemical of interest.
   a. determine if sensor displays selectivity to chemical of interest over Ascorbic acid.
   b. determine if sensor displays sensitivity to chemical of interest.
   c. add at least three increments of chemical and save response of sensor.
   d. stop pulsing current to sensor.
5. Calculate suitability of this sensor for use in the selected mode of operation.
   a. calculate linearity of the sensor.
   b. calculate sensitivity (slope of curve) of the sensor to chemical of interest.
   c. calculate selectivity of the sensor.
   d. calculate ratio of oxidation and reduction slopes.
   e. calculate ratio of true sensor response to ambient noise of the system.
   f. display calibration curves and data for sensor just calibrated.
6. Output calibration data to selected hardware.
   a. store calibration data in selected calibration data file.
   b. output data to printer or plotter.
7. Return to menu system or go to step one of FIG. 22 for next sensor.

The following is an outline of the Data Acquisition procedure correlated with the flowchart of FIG. 23.

1. Input filename for storing data.
2. Visual sensor check.
   a. initiate hardware I/O system and potentiostat to start system.
   b. determine that sensor has not broken or developed leaks.
   c. determine ambient background noise of the system for use as baseline for data collection.
   d. open data file and write calibration data to it.
3. Acquire real time data, display in near real time.
   a. turn off CPU clock
   b. read A/D signal an TTL signal, store data in memory buffer.
   c. start and display timing for data file.
   d. display oscilloscope image of sensor response.
   e. display real time clock.
   f. display real time data in near real time.
4. Initiate external event to stimulate sensor response.
   a. start external event counter.
   b. start external event timer.
   c. mark data file to signal start of response.
   d. establish new background noise baseline for sensor.
5. Pause real time data collection.
   a. stop pulsing current to sensor.
   b. display oxidation and reduction responses.
   c. display runtime data analysis of last response.
   d. display oscilloscope image of sensor response.
   e. display menu of options to change on screen, runtime parameters.
   f. if cyclic mode, display waveform at peak of response.
   g. display external event timer.
   h. display real time clock and remaining buffer size.
   i. append most recently acquired data to data file.
6. Return to step 3 and continue, or return to step 1 and start new file.
   a. initiate hardware I/O system and potentiostat to start system.
7. End real time data collection.
   a. close data file.
   b. return to menu system.

Figure 24:
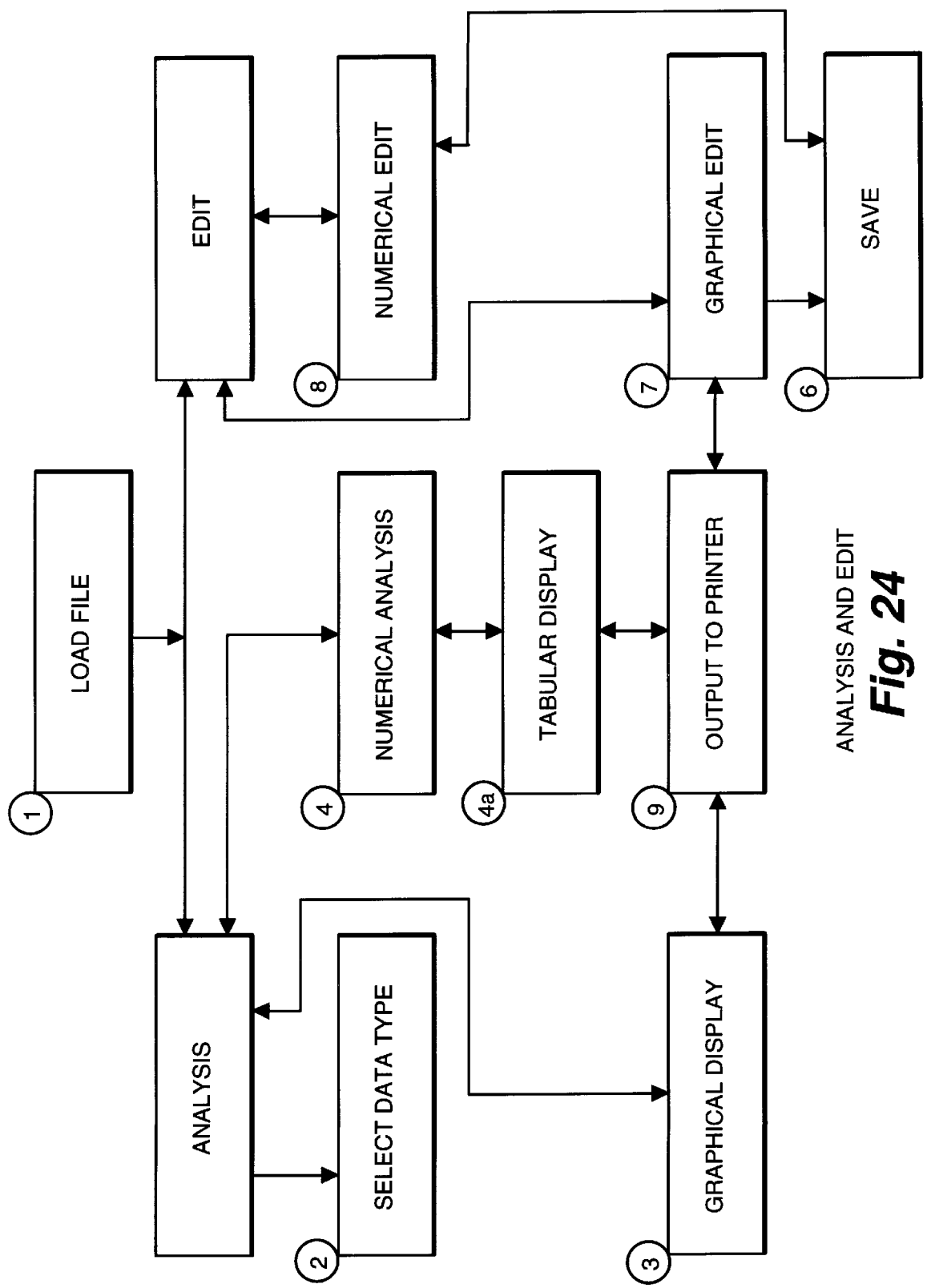
FIG. 24 is a flowchart of the automated analysis and editing procedures in the application software of the computer system of FIG. 1c.

The following is an outline of the automated Analysis and Editing pursuant to the FIG. 24 flowchart.

1. Load a data file for use in analysis and editing portions of the process.
2. Select type of data to view, all data present in the file or only events in excess of the minimum detectable limits (i.e. greater than the signal/noise ratio for this sensor and system).
3. Graphical display of data.
   a. display full screen graph of a detected event with analysis results.
   b. display multi-graph screen of four separate chemical events.
   c. scroll through data file observing specific events.
   d. output displayed data to printer or plotter.
4. Display numerical analysis of each recorded event in table form.
   a. output displayed data to printer or plotter.
   b. scroll through data file observing specific events.
5. View directory listing of all available data files, and change data directories.
6. Load or save a data file.
7. Graphical edit of a data file.
   a. move cursor through data file, adding or subtracting event markers, or data points.
   b. resave edited data file with new name.
8. Numerical edit of data file.
   a. move through data file, adding or subtracting event markers, or data points.
   b. resave edited data file with new name.
9. Output edited data files to disk storage for further analysis.

This invention has been described while making detailed reference to preferred embodiments thereof. However, since it is known that those skilled in the art, upon learning of this invention, will readily visualize yet other embodiments that are within the spirit and scope of the invention, the forgoing detailed description should not be taken as a limitation on the spirit and scope of the invention.

What is claimed is:

1. A method for measuring the concentration of a neurotransmitter in living tissue, said neurotransmitter providing oxidation and reduction chemical activity in the presence of a cyclic electrical potential, comprising the steps of;
   A—placing a microsensor at a first physical location in said tissue, said sensor being responsive to said oxidation and reduction chemical activity in said tissue,
   B—placing a reference electrode at a second physical location in said tissue,
   C—applying a cyclic electric potential selected from the group consisting of chronoamperometry and fast-cycle voltammetry to said reference electrode to produce said oxidation chemical activity in said tissue at a location generally adjacent to said microsensor, and to produce said reduction chemical activity in said tissue at said location generally adjacent to said microsensor,
   D—varying a frequency parameter of said cyclic electric potential a number of times,
   E—measuring in real time a first electrical response of said microsensor to said oxidation chemical activity during said frequency parameter variation of said cyclic electric potential,
   F—measuring in real time a second electrical response of said microsensor to said reduction chemical activity during said frequency parameter variation of said cyclic electric potential,
   G—comparing said measurements of steps E and F,
   H—generating an electrical signal as a result of step G, and
   I—identifying said neurotransmitter concentration based upon steps E and F.

2. The method of claim 1 including the step of;
   J—using said electrical signal of step H to energize a visual display in near-real time.

3. The method of claim 2 wherein said neurotransmitter is selected from the group consisting of dopamine, norepinephrine, or serotonin.

4. The method of claim 2 wherein said microsensor is responsive to a given neurotransmitter, including the step of;
   K—calibrating said microsensor to determine a response of said microsensor to different concentrations of said given neurotransmitter,
   L—storing said determined response of step K, and
   M—utilizing said stored response of step L in step I implemented by a data processing system.

5. The method of claim 4 wherein said neurotransmitter is selected from the group consisting of dopamine, norepinephrine, or serotonin.

6. The method of claim 5 including the steps of;
   N—determining a background electrical response of said microsensor, and
   O—utilizing said background response as a subtraction parameter when executing said steps E, F and I.

7. A method for measuring neurotransmitter concentration in living tissue, comprising the steps of;
   placing a microsensor at a first physical location in said tissue, said sensor being responsive to neurotransmitter chemical activity in said tissue,
   placing a reference electrode at a second physical location in said tissue,
   applying a first cyclic electric potential to said reference electrode for a first time period to produce a first chemical oxidation condition in said tissue at a location generally adjacent to said microsensor, and to produce a first chemical reduction condition in said tissue at said location generally adjacent to said microsensor,
   applying a second cyclic electric potential to said reference electrode for a second time period to produce a second chemical oxidation condition in said tissue at said location generally adjacent to said microsensor, and to produce a second chemical reduction condition in said tissue at said location generally adjacent to said microsensor,
   measuring a first electrical response of said microsensor to said first chemical oxidation condition during said first time period,
   measuring a second electrical response of said microsensor to said second chemical reduction condition during said second time period,
   identifying concentration of said neurotransmitter based upon said first and second electrical responses,
   comparing said first and second electrical responses, and
   generating an electrical signal in real time as a result of said comparing step.

8. The method of claim 7 including the step of;
   using said electrical signal to energize a visual display to visually show concentration in near-real time.

9. The method of claim 8 wherein said neurotransmitter is selected from the group consisting of dopamine, norepinephrine, apomophine, serotonin, acetaminophen, oxygen, ascorbic acid, hydrogen peroxide and nitric acid.

10. A method for measuring the chemical activity of chemicals that aid in the transmission of impulses between two living cells within a living tissue mass, comprising the steps of;

placing a microsensor at a first physical location in said tissue mass, said sensor being responsive to chemical activity within said tissue mass, placing a reference electrode at a second physical location in said tissue mass, applying a variable frequency square wave electric potential to said microsensor, said square wave having a first wave portion and a second wave portion, said first wave portion producing a chemical oxidation condition in said tissue mass at a location generally adjacent to said microsensor, said second wave portion producing a chemical reduction condition in said tissue mass at said location generally adjacent to said microsensor, varying said frequency of said square wave in N number of steps, measuring a first electrical response of said microsensor to said chemical oxidation condition for certain ones of said N steps of said square wave frequency variation, measuring a second electrical response of said microsensor to said chemical reduction condition for said certain ones of said N steps of said square wave frequency variation, said steps of measuring said first and second electrical responses of said microsensor being operable for all but a first number of said N steps of said square wave frequency variation, comparing said first and second electrical responses, and generating an electrical signal as a result of said comparing step.

11. The method of claim 10 including the step of;
using said electrical signal to energize a visual display.

12. The method of claim 11 wherein said chemicals include the group consisting of dopamine, norepinephrine, and serotonin.

13. A method for measuring neurotransmitter chemical activity in living tissue, comprising the steps of;

placing a microsensor at a first physical location in said tissue, said microsensor being responsive to neurotransmitter chemical activity within said tissue, placing a reference electrode at a second physical location in said tissue, connecting a first cyclic electric source of a first phase to said microsensor to alternately produce a first chemical oxidation condition in said tissue at a location generally adjacent to said microsensor, and a first chemical reduction condition in said tissue at said location generally adjacent to said microsensor, measuring a first electrical response of said microsensor to said first chemical oxidation condition produced by said first electric source, measuring a second electrical response of said microsensor to said first chemical reduction condition produced by said first electric source, connecting a second electric source to said microsensor to produce a second chemical reduction condition in said tissue at said location generally adjacent to said microsensor, measuring a third electrical response of said microsensor to said second chemical reduction condition produced by said second electrical source, and identifying neurotransmitter chemical activity based upon said first, second and third electrical responses.

14. The method of claim 13 including the steps of;
comparing said first, second and third electrical responses, and
generating an electrical signal as a result of said comparison.

15. The method of claim 14 including the step of;
using said electrical signal to energize a visual display.

16. The method of claim 15 wherein said neurotransmitter is selected from the group consisting of dopamine, norepinephrine, and serotonin.

17. The method of claim 14 including the steps of;
calibrating said microsensor to determine response of said microsensor to different known concentrations of said neurotransmitter, and
utilizing said determined response when comparing said first, second and third electrical responses.

18. The method of claim 17 wherein said neurotransmitter is selected from the group consisting of dopamine, norepinephrine, and serotonin.

19. Apparatus for use in measuring electrochemical activity within a living tissue mass, comprising;

a microsensor adapted to be placed at a first location within the tissue mass, said microsensor being responsive to reduction and oxidation chemical states of neurotransmitters generally adjacent to said microsensor, a reference electrode adapted to be placed at a second physical location within the tissue mass, computer means having a first input port connected to said microsensor, and having a second input port connected to said reference electrode, voltage generating means connected to said reference electrode and operable to apply a cyclic electrical voltage to said reference electrode, said voltage generating means being operable to produce an oxidation condition during a first time period, and then a reduction condition during a second time period, means including said computer means connected to said microsensor to measure a first electrochemical response of said microsensor to said oxidation condition during said first time period, and to measure a second electrochemical response of said microsensor to said reduction condition during said second time period, a visual output device connected to said computer means and controlled by said computer means, said visual output device being adapted to provide a first visual output curve in response to said first electrochemical response, and to provide a second visual output curve in response to said second electrochemical response, said first and second visual output curves having a common time origin point, impedance means adapted to be temporarily connected between said first and second input ports, manual control means operable to adjustably control timing of said computer means when said impedance means is temporarily connected between said first and second input ports, and said manual control means being adapted for manual adjustment to achieve a computer system timing wherein said first and second visual output curves overly each other to form a common curve.

* * * * *